United States Patent
Goodman et al.

(10) Patent No.: US 7,005,411 B1
(45) Date of Patent: Feb. 28, 2006

(54) METHOD FOR MODULATING NERVE CELL FUNCTION

(75) Inventors: Corey S. Goodman, Berkeley, CA (US); Thomas Kidd, Berkeley, CA (US); Guy Tear, London (GB); Claire Russell, London (GB); Kevin J. Mitchell, San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 748 days.

(21) Appl. No.: 09/191,651

(22) Filed: Nov. 13, 1998

Related U.S. Application Data

(60) Provisional application No. 60/065,543, filed on Nov. 14, 1997.

(51) Int. Cl.
*A61K 38/00* (2006.01)
*C12N 5/06* (2006.01)
*C12N 5/08* (2006.01)
*C12N 5/02* (2006.01)
*C07K 17/00* (2006.01)

(52) U.S. Cl. .......................... 514/2; 435/352; 435/353; 435/354; 435/366; 435/375; 530/350

(58) Field of Classification Search ................ 536/23.1, 536/23.7, 24.3; 435/320.1, 366, 375, 252.3, 435/352–54, 471; 530/350, 300; 514/2
See application file for complete search history.

(56) References Cited

PUBLICATIONS

Tear et al., Neuron 16(3):501–514, 1996.*
Seeger et al., Neuron 10(3):409–26, 1993.*
Oyesiku et al., J. Comp. Neurol., 364(1):68–77, 1996.*
Reinoso et al., J. Neurosci. Res., 43(4):439–53, 1996.*
Skolnick et al., Trends in Biotech., 18(1):34–39, 2000.*
WO 95 13367 A (Univ California; Univ Columbia (US)) May 18, 1995; see claims 1–10.

* cited by examiner

*Primary Examiner*—Sharon Turner
(74) *Attorney, Agent, or Firm*—Richard Aron Osman

(57) ABSTRACT

The amount of active Robo expressed on a cell is modified by modulating the effective amount of a Comm polypeptide in contact with the cell, whereby the amount of expressed active Robo is modulated inversely with the modulation of the effective amount of the Comm polypeptide in contact with the cell. In a particular embodiment, the Comm polypeptide is provided to the cell by exogenously in a pharmaceutically acceptable composition. In another aspect, the invention provides methods of screening for agents which modulate Robo-Comm interactions. These methods generally involve forming a mixture of a Robo-expressing cell, a Comm polypeptide and a candidate agent, and determining the effect of the agent on the amount of Robo expressed by the cell.

22 Claims, No Drawings

METHOD FOR MODULATING NERVE CELL FUNCTION

This application claims the benefit of U.S. Provisional Application No. 60/065,543, filed Nov. 14, 1997.

INTRODUCTION

The research carried out in the subject application was supported in part by NIH grant NS18366. The government may have rights in any patent issuing on this application.

FIELD OF THE INVENTION

The field of this invention is methods for modulating nerve cell function.

BACKGROUND

In the developing CNS, most growth cones confront the midline at one or multiple times during their journey and make the decision of whether to cross or not to cross. This decision is not a static one but rather changes according to the growth cone's history. For example, in the *Drosophila* ventral nerve cord, about 10% of the interneurons project their axons only on their own side, in some cases extending near the midline without crossing it. The other 90% of the interneurons first project their axons across the midline and then turn to project longitudinally on the other side, often extending near the midline. These growth cones, having crossed the midline once, never cross it again, in spite of their close proximity to the midline and the many commissural axons crossing it. This decision to cross or not to cross is not unique to *Drosophila* but is common to a variety of midline structures in all bilaterally symmetric nervous systems.

What midline signals and growth cone receptors control whether growth cones do or do not cross the midline? After crossing once, what mechanism prevents these growth cones from crossing again? A related issue concerns the nature of the midline as an intermediate target. If so many growth cones find the midline such an attractive structure, why do they cross over it rather than linger? Why do they leave the midline? One approach to find the genes encoding the components of such a system is to screen for mutations in which either too many or too few axons cross the midline. Such a large-scale mutant screen was previously conducted in *Drosophila*, and led to the identification of two key genes: commissureless (comm) and roundabout (robo) (Seeger et al., 1993; reviewed by Tear et al., 1993). In comm mutant embryos, commissural growth cones initially orient toward the midline but then fail to cross it and instead recoil and extend on their own side. robo mutant embryos, on the other hand, display the opposite phenotype in that too many axons cross the midline; many growth cones that normally extend only on their own side instead now project across the midline and axons that normally cross the midline only once instead appear to cross and recross multiple times (Seeger et al, 1993; present disclosure). Double mutants of comm and robo display a robo-like phenotype.

How do comm and robo function to control midline crossing? Neither the initial paper on these genes (Seeger et al., 1993) nor the cloning of comm (Tear et al., 1996) resolved this question. comm encodes a novel surface protein expressed on midline cells. In fact, the comm paper (Tear et al., 1996) ended with the hope that future work would ". . . help shed some light on the enigmatic function of Comm."

A copending application (*Robo, A Novel Family of Polypeptides and Nucleic Acids*, by inventors: Corey S. Goodman, Thomas Kidd, Kevin J. Mitchell and Guy Tear, and filed herewith) discloses the cloning and characterization of robo in various species including *Drosophila*. robo encodes a new class of guidance receptor with 5 immunoglobulin (Ig) domains, 3 fibronectin type III domains, a transmembrane domain, and a long cytoplasmic domain. Robo defines a new subfamily of Ig superfamily proteins that is highly conserved from fruit flies to mammals. The Robo ectodomains, and in particular the first two Ig domains, are highly conserved from fruit fly to human, while the cytoplasmic domains are more divergent. Nevertheless, the cytoplasmic domains contain three highly conserved short proline-rich motifs which may represent binding sites for SH3 or other binding domains in linker or signaling molecules.

For those axons that never cross the midline, Robo is expressed on their growth cones from the outset; for the majority of axons that do cross the midline, Robo is expressed at high levels on their growth cones only after they cross the midline. Transgenic rescue experiments in *Drosophila* reveal that Robo can function in a cell autonomous fashion, consistent with it functioning as a receptor. Thus, in *Drosophila*, Robo appears to function as the gatekeeper controlling midline crossing; growth cones expressing high levels of Robo are prevented from crossing the midline. Robo proteins in mammals function in a similar manner in controlling axon guidance.

Here we disclose ectopic and overexpression studies revealing that Comm down-regulates Robo expression, demonstrating that Comm functions to suppress the Robo-mediated midline repulsion. These results show that the levels of Comm at the midline and Robo on growth cones are tightly intertwined and dynamically regulated to assure that only certain growth cones cross the midline, that those growth cones that cross do not linger at the midline, and that once they cross they never do so again.

SUMMARY OF THE INVENTION

The invention provides methods and compositions for modulating the amount of active Robo expressed on a cell. The general method involves modulating the effective amount of a Comm polypeptide in contact with a cell expressing an amount of active Robo polypeptide, whereby the amount of expressed active Robo is modulated inversely with the modulation of the effective amount of the Comm polypeptide in contact with the cell. For example, where the effective amount of the Comm polypeptide is increased, the amount of expressed Robo is decreased. The Robo polypeptide is preferably a human, mouse, *C. elegans* or *Drosophila* Robo I or II sequence or a polypeptide domain thereof having a Robo-specific activity, and the Comm polypeptide specifically modulates Robo expression and (a) comprises SEQ ID NO:14 or a deletion mutant thereof which specifically modulates Robo expression and/or (b) is encoded by a nucleic acid comprising SEQ ID NO:13 or a nucleic acid which hybridizes with SEQ ID NO:13, preferably under stringent conditions. In a particular embodiment, the Comm polypeptide is provided to the cell exogenously in a pharmaceutically acceptable composition. In another aspect, the invention provides methods of screening for agents which modulate Robo-Comm interactions. These methods generally involve forming a mixture of a Robo-expressing cell, a Comm polypeptide and a candidate agent, and determining the effect of the agent on the amount of Robo expressed by the cell.

DETAILED DESCRIPTION OF THE INVENTION

The subject methods involve modulating the effective amount of a Comm polypeptide in contact with a cell expressing an amount of active Robo polypeptide, whereby the amount of expressed active Robo is modified inversely with the modulation of the effective amount of the Comm polypeptide in contact with the cell. Robo expression is found to regulate a wide variety of cell functions, including cell-cell interactions, cell mobility, morphology, etc. Accordingly, the invention provides methods for modulating targeted cell function comprising the step of modulating Robo expression by contacting the cell with a Comm polypeptide.

The targeted Robo polypeptide is generally naturally expressed on the targeted cells. The nucleotide sequences of exemplary natural cDNAs encoding *drosophila* 1, *drosophila* 2, *C. elegans*, human 1, human 2 and mouse 1 Robo polypeptides are shown as SEQ ID NOS:1, 3, 5, 7, 9, 15–16 and 11, respectively, and the full conceptual translates are shown as SEQ ID NOS:2, 4, 6, 8, 10, 17–18 and 12. The targeted Robo polypeptides comprise at least a functional domain of SEQ ID NOS:2, 4, 6, 8, 10, 17–18 and 12, which domain has Robo-specific amino acid sequence and binding specificity or function. Preferred Robo domains comprise at least 8, preferably at least 16, more preferably at least 32, most preferably at least 64 consecutive residues of one of these SEQ ID NOS. In a particular embodiment, the domains comprise one or more structural/functional Robo immunoglobulin, fibronectin or cytoplasmic motif domains described herein. The subject domains provide Robo-specific antigens and/or immunogens, especially when coupled to carrier proteins. For example, peptides corresponding to Robo- and human Robo-specific domains are covalently coupled to keyhole limpet antigen (KLH) and the conjugate is emulsified in Freunds complete adjuvant. Laboratory rabbits are immunized according to conventional protocol and bled. The presence of Robo-specific antibodies is assayed by solid phase immunosorbant assays using immobilized Robo polypeptides of SEQ ID NO:2, 4, 6, 8, 10, 17–18 or 12. Generic Robo-specific peptides are readily apparent as conserved regions in the aligned Robo polypeptide sequences of Table 1.

TABLE 1

Sequence Alignment of Robo Family Members: The complete amino acid alignment of the predicted Robo proteins encoded by drosophilia robo 1 (D1, SEQ ID NO:2) and Human robo 1 (H1, SEQ ID NO:8) are shown. The extracellular domain of C. elegans robo (CE, SEQ ID NO:6; Sax-3; Zallen et al., 1997), the extracellular domain of Drosophila robo 2 (D2, SEQ ID NO:4), and partial sequence of Human robo 2 (H2, SEQ ID NO:10) are also aligned. The D2 sequence was predicted by the gene-finder program Grail. The position of immunoglobulin domains (Ig), fibronectin domains (FN), the transmembrane domain (TM), and conserved cytoplasmic motifs are indicated. The extracellular domain of rat *robo* 1 is nearly identical to H1.

```
mH............PMHpENHAIaRSTSTTNNPSrsRSSRMWLlpAWLLLVLVASNGLP      47 D1
m.FNRKTLlCTi.llVlQA..............vIrsFCEDASNlA...............   30 CE
mKWKHVPFlVMiSllSlSpNHLFLaQLIPDPEDvErG.NDHGTPIpTSDNDDNSLGYTGS     59 H1

>IG #1
AVrGQYQSpriiehpTdlvvKknepatlnckVegKpEptiewfkdgepvStn..EKKshr    105 D1
     GENpriiehpMdTTvPknDpFtFncQaegNptptiQwfkdgRELKt...dTGshr       D2
........pViiehpIdVvvsRgSpatlncGaK.PStAKiTwykdgQpvItnkEQVNshr     81 CE
RLrQEDFPpriVehpSdlIvskgepatlnckaegRptptiewykGgeRvEtDkDdPRshr   119 H1

>IG #2
VQFKDgAlffYriMQgkkeQ..dGgEywcvaknRVgQavsrHaslqIavlrddfrvepKd   163 D1
iMlpAgGlfflkvIhSrReS..dagTywcEakneFgVaRsrnaTlqvavlrdEfrLepAN       D2
iVlDTgslfLlkvNSgkNGKDSdagAyYcvaSneHgeVKsNEGslKLaMlrEdfrvRpRT   141 CE
MLlpSgslfflriVhgrkSRP.dEgVyVcvaRnYLgeavsHnaslEvaIlrddfrQNpSd   178 H1 trvaKgeTallecgppKgIpeptLIwIkdgVplddLKAmSFGASSrVrivdggnlLiSNv   223 D1
trvaQgeValmecgAprgSpepQiswrkNgQTlNL......VGNKririvdggnlAiQEA       D2
vQALGgeMavlecSpprgFpepVVswrkdDKElRI.QDmP.....rYTLHSDgnlIiDPv   195 CE
vMvaVgePavmecQpprgHpeptiswKkdgSpldd.......KDEri.TIRggKlMiTYT   230 H1

>IG #3
EPIdEgNyKcIaQnLvgtresSYaKlIvQvkpYfMkepkdqVMLYgQTaTfHcSvggdpP   283 D1
rQsdDgRyqcvVKnVvgtresATaFlKvHvrpFLIRGpQnqtAVvgSsvVfQcrIggdpL       D2
DRsdSgTyqcvaNnmvgerVsNPaRlSvFekpKfEQepkdMtvDvgAAvLfDcrvTgdpQ   225 CE
rKsdAgKyVcvGTnmvgeresEVaElTvLerpSfVkRpSnLAvTvDDsaEfKcEARgdpV   290 H1 pKvlwkk..EEgnIpvsrA..........RiLHdEKslEiSNItpTdegTyvceaHnNvg   331 D1
pDvlwrrTASGgnmpLRKFSWLHSASGRVHVl.EdrslkLDDvtLEdmgeytceaDnAvg       D2
pQITwkr..KNEPmpvTra..........YiAKdNrGlRiERvQpSdegeyvcYaRnPAg   303 CE
pTvRwrk..DDgELpKsrY..........Ei.RddHTlkiRKvtAGdmgSytcVaEnMvg   337 H1

>IG #1
QiSaRaSlIvhappNfTKrpSnKKvGlNgVvQLPcMaSgnpPpSvfwTkegVSTlMfpn.   388 D1
GiTaTGIltvhappKfvIrpKnqLvEIgDEvLfecQaNgHpRpTLYwsVegNSSllLpGy       D2
TLeasaHlRvqappSfQTkpAdqSvPAggtAtfecTLVgQpSpaYfwskegQqDllfpsy   363 CE
KAeasaTltvqEppHfvVkpRdqVvalgrtvtfQceaTgnpqpaIfwRRegsqnllf.sy   396 H1
                       qIvaQgrtvtfPceTKgnpqpavfwQkegsqnllfpn.       H2
```

TABLE 1-continued

Sequence Alignment of Robo Family Members: The complete amino acid alignment of the predicted Robo proteins encoded by drosophilia robo 1 (D1, SEQ ID NO:2) and Human robo 1 (H1, SEQ ID NO:8) are shown. The extracellular domain of C. elegans robo (CE, SEQ ID NO:6; Sax-3; Zallen et al., 1997), the extracellular domain of Drosophila robo 2 (D2, SEQ ID NO:4), and partial sequence of Human robo 2 (H2, SEQ ID NO:10) are also aligned. The D2 sequence was predicted by the gene-finder program Grail. The position of immunoglobulin domains (Ig), fibronectin domains (FN), the transmembrane domain (TM), and conserved cytoplasmic motifs are indicated. The extracellular domain of rat robo 1 is nearly identical to H1.

```
...SsHGrQYvAADgtlQitDvrqedegyyv.cSaFSvvDssTVrVFlQvSS..vD....        440 D1
RDGRMEVTLTPEGRSVlSiARFAredSgKVvTcNalnAvgsVSsrTVVSvDt..QF....            D2
VSADGRTK..vsptgtltiEEvrqVdegAyv.cAGMnSagsslskaAlKvttKAvTGNTP        420 CE
qpPQsSsrFsvsQtgdltitnvqrsdVgyyi.cqTlnvagsiITkaYlevtd..vIA...        450 H1
qpQQPNsrCsvsptgdltitnIqrsdAgyyi.cqalTvagsilAkaQlevtd..vLT...            H2

>IG #5
erppppiiQIgpbAnqtlpKgsVaTlpcratgNpSpRiKwFHdgHAvQA.GNRYSi.iqG..       496 D1
eLppppiieqgpvnqtlpvKsIVvlpcrTLgTpvpQVswYLdgIpidVqEHERrNLsDA..            D2
AKpppTieHgHQnqtlMvgsSaIlpcQaSgKpTpGiswlRdgLpidITd..sri.sqHST        477 CE
drpppViRqgpvnqtVavdgtFvlScVatgSpvpTiLwRkdgVLvSTqd..sriK.qLeN        507 H1
drppppiiLqgpAnqtlavdgtaLcKcKatgDpLpViswlkEgFTFPGRd..PrATiq.eQ           H2

>FN #1
SslRVDdlq.lsdSgtytciasGeRgeTswAaTltveKpgs..TSLHraAdpstypAppg        553 D1
gAlTiSdlqrHEdEgLytcvasnRNgKsswsGylRLDTptNpNiKfFrapElstypgppg            D2
gslHiAdl.kKPdtgVytciaKneDgestwsaSltveDHtsN.AqfVrMpdpsNFpsSpT        535 CE
gvlqiR.YAklGdtgRytciasTPsgeatwsayIEvvQeFgVp.VqPPrPTdpNLIpsAps       565 H1
gTlqiKNl.rIsdtgtytcvaTSSsgeaswsaVlDvTeSgAT.i..SKNYdlsDLpgpps            H2

TpKvLnvsrtsISlRwAKSqEKPGAVgpIi..gyTVeyfspdlQTgwIVAaHrvGDtQVti       612 D1
kpqMvEKGEnsvtlsw...TRSNKVggSSLVgyVieMfGKNETDgwVAvGTrvQNttFtQ           D2
QpIIvnvtDtEvElHw...NAPSTsgaGpitgyiiQyYspdlgQTwFNIPDYvAStEyRi       592 CE
kpEvtdvsrnTvtlsw...qpNLNsgaTp.tSyiieafsHASgSswqtvaENvktEtSAi       621 H1
kpqvtdvtKnsvtlsw...qpGTPGTLpA.SAyiieafsQSVSNswqtvaNHvkttLytV           H2

>FN #2
SglTpgtsyVflvraenTQgisvpsGLsNViktIEA....DfDAASANdlsAarT.llTg        667 D1
TglLpgVNyFflirraenSHgLsLpsPMsEpitVGTR....YfNS..gLdlsEarASllsg           D2
kglkpSHsyMfViraenEkgiGTpsVSsALvttSKPAAQVAlSDKNKMdMAIaEKRlTsE        652 CE
kglkpnAiylflvraAnAYgisDpsqIsDpvktQDV.....lPTSQgVdHKQVQRE.lGN        675 H1
RglRpntiylfMvraInPkV.svT.q                                               H2

KSvelIDasAinAsavrlEwMLHvSADEkyvegLRiHyK..DaSVPSAQYHSITvMDAsa        725 D1
DvvelSnasvVDstsMKlTwQI...INGkyvegFyVYArQLPnPLNTKyRMLTILNGGGa            D2
QLIKlEEVKTinstavrlFwKKR..KLEELiDgyyiKWrGPpRTNDNQyVN...vTSpsT       707 CE
AvLHlHnPTvLSsssIEVHwT..vDQQSQyiQgyKiLyrPSGaNHGESDWLVFEvRTpAK       733 H1

>FN #3
esFvvGnlKkytKyeffLTpf...fETiegQpsnskTaltYedvpsappDNIQiGmYn..        780 D1
SsCTiTGlVQytLyeffIVpf...YKsVegKpsnsRIaRtledvpsEApYgMEALLln..            D2
eNYvvSnlMPFtnyeffVIpYHSGVHsiHgapsnsMDVltAeAPpsLppEDvRiRmlnL.        766 CE
NsVviPDlRkGVnyeIKARpf...fNEFQgaDsEIkFaKtleEApsappQgvTVSKNDGN       790 H1

QtaGWvRwTpppSQHHngNlYgykiEVSAgnTM.....KVlAnMtLnaTtTsvLlNnltt       835 D1
SSaVFLKwkapELKGRHgVlLNyH.vivRgIDtAHNFSRIlTnVtIdaASPTLvlAnlTE           D2
.tTLRIswkapKAdGIngIlKgFQiviv.gQAPNNR.....nItTnERAAsvTlFHlVt        819 CE
GtaILvswQpppEdTQngMVQEykV.WCLgnEtR.....YHInKtVdGStFsvvIPFlVP       844 H1

<
gAVysvrLNSFtKagDgpysKpIslFMdpTHHVHPpRAHPsGTHDGRHEGqDLTYHNNgN        895 D1
gVMyTvGvaaGNnagvgpyCVpATlRldpITKRLDpFINQRDHVND..............            D2
gMTyKIrvAARsnGgvgv..........ShgTSEVIMNqDTlEKHL.AAQgENESFLYgL       868 CE
gIRysvEvaaStGagSgvKsEpQFIQldAhgNPVSpEDqVslAQQI..............       890 H1

>                 TM            <
iPPGDINPTTHKKTTdYlSGpwLMViVCiVlLvlVisAAIsM.vyFkrkhQmTKElGHLS       954 D1
..............vlTqpwFIiiLgAilavlMLs..fGAMvFVkrkhMm..MkQsAL           D2
iNK..............SHVpVIViVaILiIFvViiIAY.CYwRNS...gkDRSF           909 CE
..............SdvVKqp..AFiagiGAaCWiiLMVfsIwLyRHrkKR..NglTsTY       932 H1

VVSDNEIT.................AlniNSKESL.wIDHHRGwRTADTDKD..             988 D1
AGIRKVPSFTFTPTVTYQRGGEAVSSGGRPGLlniSEPAAQPwLAD..TwPNTGNNHNDC       990 H1

........SgLsEsKlLSHVNSSQ..SnynnS..........DGGtDyAEvd....TRNL      1024 D1
SISCCTAGNgNsDslTTYSRPADCIAnynnQLDNKQTNLMLPEStVyGDvdLSNKINEM      1050 H1
```

TABLE 1-continued

Sequence Alignment of Robo Family Members: The complete amino acid alignment of the predicted Robo proteins encoded by drosophilia robo 1 (D1, SEQ ID NO:2) and Human robo 1 (H1, SEQ ID NO:8) are shown. The extracellular domain of C. elegans robo (CE, SEQ ID NO:6; Sax-3; Zallen et al., 1997), the extracellular domain of Drosophila robo 2 (D2, SEQ ID NO:4), and partial sequence of Human robo 2 (H2, SEQ ID NO:10) are also aligned. The D2 sequence was predicted by the gene-finder program Grail. The position of immunoglobulin domains (Ig), fibronectin domains (FN), the transmembrane domain (TM), and conserved cytoplasmic motifs are indicated. The extracellular domain of rat robo 1 is nearly identical to H1.

```
        CYTOPLASMIC MOTIF #1
TtfYNCR.......KSPDNptpyattMIiGTS........sSETCTkT.TSISADkDSGT    1068 D1
KtfNSPNLKDGRFVNPSGQptpyattQLiQSNLSNNMNNGsGDSGEkHWKPLGQQkQEVA    1110 H1
HSPyS........DAFAGQVPAVpVV..KSNyLqYPVEP.....................    1097 D1
PVQyNIVEQNKLNKDYRANDTVPpTIPYNQSyDqNTGGSYNSSDRGSSTSGSQGHKKGAR    1170 H1

CYTOPLASMIC MOTIF #2
.........InwSEFlppppEhppp...sSTy......GyAqGSp...............    1124 D1
TPKVPKQGGMnwADLlppppAhpppHSNsEEyNISVDESyDqEMpCPVPPARMYLQQDEL    1230 H1

..eSSRKSSKSAGSgISTNQSILNAsIHsSSSGGFsAWGVSPQYAVAcp...........    1171 D1
EEeEDERGPTPPVRgAASSPAAVSYsHQsTATLTPsPQEELQPMLQDcpEETGHMQHQPD    1290 H1

................pENVy...sNpl.....SAVAGGTQNRYQITPTNQHPPQl....    1203 D1
RRRQPVSPPPPPRPISpPHTyGYIsGplVSDMDTDAPEEEEDEADMEVAKMQTRRlLLRG    1350 H1

....paY................FATTGPGGAVPPNHLP.............faTQRHaa    1230 D1
LEQTpaSSVGDLESSVTGSMINGWGSASEEDNISSGRSSVSSSDGSFFTDADfaQAVAaa    1410 H1

SeyQaglNAar................cAQSRACNsCdALATPSPmq.............    1261 D1
Aey.aglKVarRQMQDAAGRRHFHASQcPRPTSPVsTdSNMSAAVmqKTRPAKKLKHQPG    1469 H1

CYTOPLASMIC MOTIF #3
...........ppppvpVpEGWYQPVHPNSH.PMHpTS.SNHQIYQCSSECsDHSRSsQS    1307 D1
HLRRETYTDDLppppvpPpAIKSPTAQSKTQLEVRpVVVPKLPSMDARTDRsSDRKGsSY    1529 H1

HKrQL..................QLEeHGSSAkQrgGHHRRrA.pVVQPCMESeN......ENM    D1
KGrEVLDGRQVVDMRTNPGDPREAQeQQNDGkGrgNKAAKrDLpPAKTHLIQeDILPYCRPTF    H1

LAEYEQrQYTsDCCNssrEGDTC..........SCSeGSCl..yAeAgePAPRQMTAKNT    1395 D1
PTSNNPrDPSsSSSMssrGSGSRQREQANVGRRNIAeMQVlGGy.eRgeDNNEELEETES    1651 H1
```

Exemplary such Robo specific immunogenic and/or antigenic peptides are shown in Table 2.

TABLE 2

Immunogenic Robo polypeptides eliciting Robo-specific rabbit polyclonal antibody: Robo polypeptide-KLH conjugates immunized per protocol described below.

| Robo Polypeptide, Sequence | Immunogenicity |
| --- | --- |
| SEQ ID NO:2, residues 68–77 | +++ |
| SEQ ID NO:2, residues 79–94 | +++ |
| SEQ ID NO:2, residues 95–103 | +++ |
| SEQ ID NO:2, residues 122–129 | +++ |
| SEQ ID NO:2, residues 165–176 | +++ |
| SEQ ID NO:2, residues 181–191 | +++ |
| SEQ ID NO:2, residues 193–204 | +++ |
| SEQ ID NO:2, residues 244–251 | +++ |
| SEQ ID NO:2, residues 274–290 | +++ |
| SEQ ID NO:2, residues 322–331 | +++ |
| SEQ ID NO:2, residues 339–347 | +++ |
| SEQ ID NO:2, residues 407–417 | +++ |
| SEQ ID NO:2, residues 441–451 | +++ |
| SEQ ID NO:2, residues 453–474 | +++ |
| SEQ ID NO:2, residues 502–516 | +++ |
| SEQ ID NO:2, residues 541–553 | +++ |
| SEQ ID NO:2, residues 617–629 | +++ |

In addition, species-specific antigenic and/or immunogenic peptides are readily apparent as diverged extracellular or cytosolic regions in Table 1. Human Robo-specific antibodies are characterized as uncross-reactive with non-human Robo polypeptides (SEQ ID NOS:2, 4, 6 and 12). Exemplary such human specific peptides are shown in Table 3.

TABLE 3

Immunogenic Robo polypeptides eliciting human Robo-specific rabbit polyclonal antibody: Robo polypeptide-KLH conjugates immunized per protocol described below (some antibodies show cross-reactivity with corresponding mouse/rat Robo polypeptides).

| Robo Polypeptide, Sequence | Immunogenicity |
| --- | --- |
| SEQ ID NO:8, residues 1–12 | +++ |
| SEQ ID NO:8, residues 18–28 | +++ |
| SEQ ID NO:8, residues 31–40 | +++ |
| SEQ ID NO:8, residues 45–65 | +++ |
| SEQ ID NO:8, residues 106–116 | +++ |
| SEQ ID NO:8, residues 137–145 | +++ |
| SEQ ID NO:8, residues 174–184 | +++ |
| SEQ ID NO:8, residues 214–230 | +++ |
| SEQ ID NO:8, residues 274–286 | +++ |
| SEQ ID NO:8, residues 314–324 | +++ |
| SEQ ID NO:8, residues 399–412 | +++ |
| SEQ ID NO:8, residues 496–507 | +++ |
| SEQ ID NO:8, residues 548–565 | +++ |
| SEQ ID NO:8, residues 599–611 | +++ |
| SEQ ID NO:8, residues 660–671 | +++ |
| SEQ ID NO:8, residues 717–730 | +++ |
| SEQ ID NO:8, residues 780–791 | +++ |
| SEQ ID NO:8, residues 835–847 | +++ |

TABLE 3-continued

Immunogenic Robo polypeptides eliciting human Robo-specific rabbit polyclonal antibody: Robo polypeptide-KLH conjugates immunized per protocol described below (some antibodies show cross-reactivity with corresponding mouse/rat Robo polypeptides).

| Robo Polypeptide, Sequence | Immunogenicity |
| --- | --- |
| SEQ ID NO:8, residues 877–891 | +++ |
| SEQ ID NO:8, residues 930–942 | +++ |
| SEQ ID NO:8, residues 981–998 | +++ |
| SEQ ID NO:8, residues 1040–1051 | +++ |
| SEQ ID NO:8, residues 1080–1090 | +++ |
| SEQ ID NO:8, residues 1154–1168 | +++ |
| SEQ ID NO:8, residues 1215–1231 | +++ |
| SEQ ID NO:8, residues 1278–1302 | +++ |
| SEQ ID NO:8, residues 1378–1400 | +++ |
| SEQ ID NO:8, residues 1460–1469 | +++ |
| SEQ ID NO:8, residues 1497–1519 | +++ |
| SEQ ID NO:8, residues 1606–1626 | +++ |
| SEQ ID NO:8, residues 1639–1651 | +++ |
| SEQ ID NO:10, residues 5–16 | +++ |
| SEQ ID NO:10, residues 38–47 | +++ |
| SEQ ID NO:10, residues 83–94 | +++ |
| SEQ ID NO:10, residues 112–125 | +++ |
| SEQ ID NO:10, residues 168–180 | +++ |
| SEQ ID NO:10, residues 195–209 | +++ |
| SEQ ID NO:10, residues 222–235 | +++ |
| SEQ ID NO:10, residues 241–254 | +++ |

The subject domains provide Robo domain specific activity or function, such as Robo-specific cell, especially neuron modulating or modulating inhibitory activity, Robo-ligand-binding or binding inhibitory activity. Robo-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Robo regulating protein or other regulator that directly modulates Robo activity or its localization; or non-natural binding target such as a specific immune protein such as an antibody, or a Robo specific agent such as those identified in screening assays such as described below. Robo-binding specificity may be assayed by binding equilibrium constants (usually at least about $10^7 M^{-1}$, preferably at least about $10^8 M^{-1}$, more preferably at least about $10^9 M^{-1}$), by the ability of the subject polypeptide to function as negative mutants in Robo-expressing cells, to elicit Robo specific antibody in a heterologous host (e.g a rodent or rabbit), etc.

Similarly, the Comm polypeptide is conveniently selected from Comm polypeptides which specifically modulate Robo expression. Exemplary suitable Comm polypeptides (a) comprise SEQ ID NO:14 or a deletion mutant thereof which specifically modulates Comm expression and/or (b) are encoded by a nucleic acid comprising SEQ ID NO:13 or a nucleic acid which hybridizes with SEQ ID NO:13 under stringent conditions. Suitable deletion mutants are readily screened in Robo down-regulations assays as described below. Preferred Comm domains comprise at least 8, preferably at least 16, more preferably at least 32, most preferably at least 64 consecutive residues of SEQ ID NO:14 and provide a Comm specific activity, such as Comm-specific antigenicity and/or immunogenicity, especially when coupled to carrier proteins as described above for Robo. Exemplary such Comm specific immunogenic and/or antigenic peptides are shown in Table 4.

TABLE 4

Immunogenic Comm polypeptides eliciting Comm-specific rabbit polyclonal antibody: Comm polypeptide-KLH conjugates immunized per protocol described above.

| Comm Polypeptide, Sequence | Immunogenicity |
| --- | --- |
| SEQ ID NO:14, residues 1–11 | +++ |
| SEQ ID NO:14, residues 6–17 | +++ |
| SEQ ID NO:14, residues 18–34 | +++ |
| SEQ ID NO:14, residues 35–44 | +++ |
| SEQ ID NO:14, residues 45–63 | +++ |
| SEQ ID NO:14, residues 64–73 | +++ |
| SEQ ID NO:14, residues 74–891 | +++ |
| SEQ ID NO:14, residues 92–109 | +++ |
| SEQ ID NO:14, residues 110–126 | +++ |
| SEQ ID NO:14, residues 127–136 | +++ |
| SEQ ID NO:14, residues 137–151 | +++ |
| SEQ ID NO:14, residues 152–171 | +++ |
| SEQ ID NO:14, residues 172–185 | +++ |
| SEQ ID NO:14, residues 186–199 | +++ |
| SEQ ID NO:14, residues 200–215 | +++ |
| SEQ ID NO:14, residues 216–235 | +++ |
| SEQ ID NO:14, residues 236–250 | +++ |
| SEQ ID NO:14, residues 251–260 | +++ |
| SEQ ID NO:14, residues 261–275 | +++ |
| SEQ ID NO:14, residues 276–288 | +++ |
| SEQ ID NO:14, residues 289–307 | +++ |
| SEQ ID NO:14, residues 308–317 | +++ |
| SEQ ID NO:14, residues 318–331 | +++ |
| SEQ ID NO:14, residues 332–344 | +++ |
| SEQ ID NO:14, residues 345–356 | +++ |
| SEQ ID NO:14, residues 357–370 | +++ |
| SEQ ID NO:14, residues 41–153 | +++ |
| SEQ ID NO:14, residues 117–329 | +++ |

The subject domains provide Comm domain specific activity or function, such as Comm-specific cell, especially neuron modulating or modulating inhibitory activity, Comm-ligand-binding or binding inhibitory activity. Comm-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Comm regulating protein or other regulator that directly modulates Comm activity or its localization; or non-natural binding target such as a specific immune protein such as an antibody, or a Comm specific agent such as those identified in screening assays such as described below. Comm-binding specificity may be assayed by binding equilibrium constants (usually at least about $10^7 M^{-1}$, preferably at least about $10^8 M^{-1}$, more preferably at least about $10^9 M^{-1}$), by the ability of the subject polypeptide to function as negative mutants in Comm-expressing cells, to elicit Comm specific antibody in a heterologous host (e.g a rodent or rabbit), etc.

In one embodiment, the Comm polypeptides are encoded by a nucleic acid comprising SEQ ID NO:13 or a nucleic acid which hybridizes with a full-length strand of SEQ ID NO:13, preferably under stringent conditions. Such nucleic acids are at least 36, preferably at least 72, more preferably at least 144 and most preferably at least 288 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE (Conditions I); preferably hybridizing in a buffer comprising 50% formamide in 5×SSPE buffer at a temperature of 42° C. and remaining bound when subject to washing at 42° C. with 0.2×SSPE buffer at 42° C.

(Conditions II). Exemplary nucleic acids which hybridize with a strand of SEQ ID NO:13 are shown in Table 5.

TABLE 5

Exemplary nucleic acids which hybridize with a strand of SEQ ID NO:13 under Conditions I and/or II.

| Comm Nucleic Acids | Hybridization |
| --- | --- |
| SEQ ID NO:13, nucleotides 1–47 | + |
| SEQ ID NO:13, nucleotides 58–99 | + |
| SEQ ID NO:13, nucleotides 95–138 | + |
| SEQ ID NO:13, nucleotides 181–220 | + |
| SEQ ID NO:13, nucleotides 261–299 | + |
| SEQ ID NO:13, nucleotides 274–315 | + |
| SEQ ID NO:13, nucleotides 351–389 | + |
| SEQ ID NO:13, nucleotides 450–593 | + |
| SEQ ID NO:13, nucleotides 524–546 | + |
| SEQ ID NO:13, nucleotides 561–608 | + |
| SEQ ID NO:13, nucleotides 689–727 | + |
| SEQ ID NO:13, nucleotides 708–737 | + |
| SEQ ID NO:13, nucleotides 738–801 | + |
| SEQ ID NO:13, nucleotides 805–854 | + |
| SEQ ID NO:13, nucleotides 855–907 | + |
| SEQ ID NO:13, nucleotides 910–953 | + |
| SEQ ID NO:13, nucleotides 1007–1059 | + |

A wide variety of cell types express Robo polypeptides subject to regulation by the disclosed methods, including many neuronal cells, transformed cells, infected (e.g. virus) cells, etc. Ascertaining Robo expression is readily effected by antibody staining. Accordingly, indications for the subject methods encompass a wide variety of cell types and function, including axon outgrowth, tumor cell invasion or migration, etc. The target cell may reside in culture or in situ, i.e. within the natural host. For in situ applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Comm polypeptides may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic polypeptides. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts.

In one embodiment, the invention provides administering the subject Comm polypeptides in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations for polypeptide-based therapeutics are known in the art. The compositions may be provided in any convenient form including tablets, capsules, troches, powders, sprays, creams, etc. As such the compositions, in pharmaceutically acceptable dosage units or in bulk, may be incorporated into a wide variety of containers. For example, dosage units may be included in a variety of containers including capsules, pills, etc. The compositions may be advantageously combined and/or used in combination with other therapeutic or prophylactic agents, different from the subject compounds. In many instances, administration in conjunction with the subject compositions enhances the efficacy of such agents, see e.g. Goodman & Gilman's The Pharmacological Basis of Therapeutics, $9^{th}$ Ed., 1996, McGraw-Hill.

In another aspect, the invention provides methods of screening for agents which modulate Robo-Comm interactions. These methods generally involve forming a mixture of a Robo-expressing cell, a Comm polypeptide and a candidate agent, and determining the effect of the agent on the amount of Robo expressed by the cell. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Cell and animal based neural guidance/repulsion assays are described in detail in the experimental section below.

The following experimental section and examples are offered by way of illustration and not by way of limitation.

Experimental roundabout is Required to Prevent Ipsilateral Axons from Crossing the Midline. Mutations in robo lead to an increase in the number of embryonic CNS axons in the commissures, coincident with a reduction of the number of axons in the longitudinal connectives as observed with MAb BP 102. The two commissures are thicker than normal and partially fuse as they spill over into one another; the longitudinals are thinner and pulled closer together toward the midline. We analyzed the robo mutant phenotype in more detail using the 1 D4 MAb (anti-Fas II) which at stage 13 stains a subset of growth cones (including aCC, pCC, vMP2, MP1, dMP2) and from stages 14–17 stains three major longitudinal axon tracts, including (from medial to lateral) the pCC pathway (pioneered by the pCC growth cone), the MP1 pathway (pioneered by the MP1 growth cone), and a 3rd lateral pathway (Lin et al., 1994; Hidalgo and Brand, 1997). Previous analysis (Seeger et al., 1993) with MAb 1D4 showed that the pCC growth cone, which normally projects anteriorly on its own side near the midline to pioneer the pCC pathway, in robo mutant embryos projects across the midline, fasciculating with its contralateral homologue at the midline. The axon pathway it pioneers—the pCC pathway—which normally projects longitudinally on its own side near the midline, in robo mutant embryos projects back and forth across the midline. The pCC pathway takes on a circular pattern as it joins with the same pathway from the other side and whirls back and forth across the midline, thus defining the phenotype for which the gene was named.

The fuzzy commissure phenotype observed in robo mutant embryos does not appear to be due to changes in cell fates at the midline or elsewhere in the CNS. All of the midline cells are present, and their fates appear normal as assayed with a variety of different markers (Seeger et al., 1993). All of the commissural and longitudinal axon pathways begin in their normal location, but the longitudinal pathways are pulled closer at the midline as axon bundles circle around the midline, and the commissures become fused and fuzzy as too many axons cross the midline. In contrast, in mutants in which all or some of the midline cells die or fail to properly differentiate, the longitudinal pathways either collapse onto the midline or from the outset form closer together than normal (Klämbt et al., 1991; Mayer and Nüsslein-Volhard, 1988). Thus, the defects observed in robo mutant embryos are not due to changes in cell fates but rather result from defects in axon guidance.

We examined in greater detail the behavior of the pCC growth cone in robo mutant compared to wild type embryos. In wild type embryos, the vMP2 cell body lies embedded at the edge of the midline. The pCC growth cone extends anterior to a point just lateral to vMP2's cell body. The pCC growth cone is then met by the lateral extension of vMP2's growth cone, and as pCC extends anteriorly and a bit laterally, the vMP2 growth cone wraps around pCC's axons and extends right behind it (Lin et al., 1994). This tight association of vMP2 and pCC is mediated by Fasciclin II (Fas II), a homophilic cell adhesion molecule (CAM) (Grenningloh et al., 1990, 1991) that is expressed from the beginning of axon outgrowth on the cell bodies, axons, and growth cones of a subset of neurons, including pCC and vMP2. In FasII mutant embryos, vMP2 and pCC no longer tightly associate, and their axons fail to fasciculate (Lin et al., 1994).

If the pCC and vMP2 neurons express Fas II, and their growth cones and axons are so attracted to each other in a Fas II-mediated fashion, why does not pCC's growth cone initially extend more medially toward vMP2's cell body which is a short distance away? The answer appears to be because vMP2's cell body is partly embedded in other midline cells, and thus vMP2's cell body is partly surrounded by the putative midline repellent. In robo mutant embryos, pCC's initial trajectory is directly toward vMP2's cell body, where it adheres to vMP2; pCC's growth cone then crosses the midline, fasciculating with its contralateral homologue at the midline.

roundabout is Required to Prevent Commissural Axons from Recrossing the Midline. The circular pathway taken by the pCC pathway as it crosses back and forth across the midline (as visualized with the anti-Fas II MAb) led us to suggest that some axons were freely recrossing the midline. Although Fas II is expressed on a relatively small subset of axons in the early embryo, and thus we can use it to observe pCC's growth cone abnormal crossing of the midline in robo mutants, the resulting pattern of expression in older embryos becomes quite complicated and it is difficult to resolve precisely which axons are crossing the midline.

To confirm that axons cross and recross the midline freely in robo mutants, we examined the expression of Connectin (Nose et al., 1992), a CAM expressed on a more restricted subset of CNS axons than is Fas II. Connectin is also expressed on motor axons in the segmental nerve. We used the C1.427 MAb to follow Connectin expression (Meadows et al., 1994). Connectin is expressed on the SP1 neuron whose cell body lies near the midline just anterior to the anterior commissure, and just medial to the longitudinal tracts. SP1's growth cone normally projects across the midline, fasciculating with the axon of its contralateral homologue. The growth cone then appears to adhere to the cell body of its contralateral homologue, grows around that cell body, and turns to project anteriorly in a medial subfascicle of the pCC pathway.

In robo mutant embryos as in wild type embryos, SP1's growth cone extends across the midline, adheres to the axon and then cell body of its contralateral homologue, and turns to project anteriorly. However, as it extends anteriorly into the next segment, it typically moves toward the midline, apparently attracted towards and adhering to the axon of its contralateral homologue just on the other side of the midline. The two SP1 axons typically join together around the posterior commissure of the next anterior segment. Sometimes they extend together on the left side of the midline and sometimes on the right side, freely crossing and recrossing the midline while fasciculating with the SP1 axons originating from both sides of neighboring segments. These results show that in addition to preventing ipsilaterally projecting axons from crossing the midline, Robo also functions to prevent contralaterally projecting axons from recrossing the midline.

roundabout Controls Crossing of the midline in a Dosage Sensitive Manner. Another axonal marker which labels a very small subset of axons is the Tau-β-galactosidase reporter gene expressed under control of the apterous promoter (called apC; Lundgren et al., 1995). In wild type embryos, the apC-tau-lacZ transgene labels three interneurons per abdominal hemisegment, here called the Ap neurons. The Ap neurons have lateral cell bodies and their growth cones initially project towards the midline. Upon nearing the midline, these growth cones then turn to project anteriorly on their own side along the edge of the midline, fasciculating with each other and with their homologues from neighboring segments; in wild type embryos, they never cross the midline in abdominal segments.

In robo mutant embryos, the Ap axons cross the midline in every segment, join up with their contralateral homologues, and often project anteriorly in one discrete longitudinal fasicle. The Ap fascicle displays two behaviors, usually crossing and recrossing the midline multiple times as a single bundle, or occasionally separating into different bundles of axons which project on one side or the other and independently cross the midline.

We observed a partially penetrant Ap axon phenotype in robo heterozygous embryos. In wild type, none of the 6 Ap axons in each segment ever cross the midline; in robo homozygous mutants, all 6 Ap axons cross the midline. In robo heterozygous mutant embryos, one of the Ap axons is observed crossing the midline in about 30% of segments, which accounts for a penetrance of about 5% of all Ap axons (Table 1). This partially penetrant crossing with 50% of robo indicates a dose requirement for the robo gene product in these axons. Moreover, since the Ap axons extend midway through axonogenesis, once many axon pathways have already been pioneered, these results indicate that robo is required throughout axonogenesis, not just to establish the initial projections of the pioneer axons.

Underexpression of Comm Leads to Increased Levels of Robo Protein. The commissureless (comm) mutant has a complementary phenotype to that of robo in that too few axons cross the midline (Seeger et al., 1993). When visualised with MAb BP102, the axon commissures are noticeably absent. In certain hypomorphic comm alleles (e.g., comm[7]; Tear et al., 1996), the commissures are not completely absent, but rather partial and highly abnormal axon commissures do form in a few segments (particularly in the thorax). We examined the expression of Robo protein in these comm hypomorphic alleles using the 13C9 anti-Robo MAb (Kidd et al, 1997). Normally, Robo is expressed at very low levels on commissural axons and at high levels on longitudinal axons. In comm mutant embryos, Robo expression in the longitudinal tracts appears even higher than normal. Interestingly, in comm hypomorphic alleles, the occasional thin commissures express Robo protein at levels that are higher than normally seen in the commissures and closer to what is typically seen in the longitudinal tracts. This result was our first hint that Comm protein might function by suppressing Robo expression on commissural axons. Previous studies had shown that comm encodes a novel transmembrane protein that is expressed by the midline glia and that is apparently transferred to commissural axons (Tear et al., 1996). Given these results, we wondered whether expression of comm in all neurons might reduce Robo levels and lead to a robo phenotype.

Overexpression of Comm generates a robo-Like Phenotype. To test the hypothesis that increased expression of comm might lead to a robo-like phenotype, we used the UAS-GAL4 system (Brand and Perrimon, 1993) to change the pattern of comm expression. We generated UAS-comm transgenic lines and drove expression pan-neurally using the sca-GAL4 line. Since flies carrying a copy of both the driver and effector transgenes are viable, we used them as parents and examined their progeny. A continuous range of robo-like phenotypes was observed with MAbs BP102 and 1 D4. The range of phenotypes reveals the comm gain-of-function phenotype to be dosage sensitive, as the severity increased in embryos carrying two copies of both transgenes as compared to embryos carrying only one copy of each.

Superficially, the robo phenotype can be mimicked by mutants causing inappropriate migration or cell death of the midline glia, both of which result in fuzzy commissures (Klämbt et al., 1991). However, such phenotypes are not visible until midway through axonogenesis, and are easily detected by examining early axon behavior. In addition, we stained the embryos with a MAb raised against 8H 11, a protein expressed specifically by the midline glia, and confirmed that the midline glia are still present In the embryos ectopically expressing comm, Fas II positive axons, such as pCC, were found to behave identical to how they behave in robo mutants. When Comm is overexpressed, the pCC growth cone extends towards the vMP2 cell body, and then across the midline, just as it does in a robo mutant. In the comm gain-of-function, the pCC fascicle freely crosses and midline and forms the same circles or whirls as it does in the robo loss-of-function.

Overexpression of Comm Leads to Reduced Levels of Robo Protein. Having established that the comm overexpression generates a bona fide robo-like axon guidance phenotype, we next examined Robo expression in these embryos using the anti-Robo MAb 13C9. The sca-GAL4 driver begins driving expression in the neuroepithelium before axon outgrowth (~stage 9) has begun and switches off by stage 13; sca-GAL4 does not express in the epidermis. In wild type embryos, the pattern of Robo protein expression begins in the neuroepithelium, as well in some lateral epidermal stripes, but is conspicuously absent from the midline region. In comm gain-of-function embryos, Robo expression in the neuroepithelium is greatly reduced or absent, while the epidermal expression outside the nervous system is maintained. This same pattern can be observed around the time when the first growth cones are extending. In wild type embryos during stages 12 and 13, no Robo is seen at the midline, but there is a high level of Robo expression on ipsilaterally projecting growth cones such as pCC and a significant level throughout the neuroepithelium. In contrast, in comm gain-of-function embryos, the pCC growth cone lacks Robo protein and the neuroepithelium expresses greatly reduced levels of Robo.

The dramatic reduction in the levels of Robo were observed until about stage 14, coincident with the sca-GAL4 driver ceasing expression. In the sca-GAL4; UAS-robo embryos, Robo protein begins to accumulate throughout the CNS after stage 14, reaching significant levels (but still below wild type) by stage 16. Interestingly, in these transgenic embryos, although we observe some Robo-positive axons in the commissures at later stages, Robo expression remains higher in longitudinal tracts. We interpret the Robo-positive axons in the commissures as later axons following misguided pioneer axons; fasciculation with the pioneers allows these Robo-positive axons to cross the midline in spite of modest levels of Robo.

The elav-GAL4 line also expresses pan-neurally but only in post-mitotic neurons; it begins driving expression of UAS transgenes during stage 12 and remains expressed throughout the rest of embryogenesis. Ectopic expression of comm by elav-GAL4 led to a less severe version of the robo phenotype. We interpret this weaker phenotype as being due to either a weaker overall level of Comm expression or because increased Comm initiates after the pioneers have already established the initial pathways. In addition, since sca-GAL4 drives expression in midline glia, the source of normal comm expression, while elav-GAL4 does not drive expression in the midline glia, the possibility exists that the less severe phenotype of the elav transgene is due to this lack of midline comm expression.

To address this issue, we attempted to increase the level of Comm specifically at the midline using multiple GAL4 lines, including sim-GAL4, slit-GAL4, F63-GAL4, and p52A-GAL4, all of which express at the midline during the period of commissure formation. When UAS-comm was expressed by any of these four lines, only very weak BP 102 phenotypes were observed, although because most of these inserts are homozygous lethal, we have not been able to easily increase the dosage with these lines to comparable levels as with the sca-GAL4 line. None of these gain-of-function phenotypes was as strong as that observed with the sca-GAL4 line. We also cannot rule out that these differences in the strength of the gain-of-function phenotypes using different GAL4 lines do not reflect differences in timing, levels of expression, or location of expression within the CNS.

We conclude that the normal function of comm is to down-regulate the low level of Robo expression present on commissural axons, thereby allowing them to cross the midline. Increasing levels of Comm in the CNS lead to more severe robo-like phenotypes, indicating a dosage sensitivity. This sensitivity to dosage is also reflected in the behavior of Ap axons in robo heterozygotes, thus showing a parallel dosage sensitivity by either decreasing Robo or increasing Comm.

These results indicate that control of Robo expression is complex and highly regulated from transcription to translation to post-translational. We show that there is an inverse correlation between Comm expression and Robo expression. In wild type embryos, Comm is expressed at the midline, and Robo expression is very low on commissural axons crossing the midline. In comm hypomorphic mutant embryos, those few axons that do cross the midline now express higher levels of Robo protein. In comm gain-of-function embryos (using transgenic constructs that drive over- and ectopic expression of comm), the overall levels of Robo are dramatically decreased wherever increased Comm expression coincides with Robo expression. Furthermore, using certain GAL4 lines that drive transient comm expression, we observe that once Comm disappears in older embryos, Robo protein expression begins to increase towards its normal levels. Thus, Comm down-regulates Robo expression in a very tight fashion.

Only a small amount of Comm is normally expressed at the midline. The midline also expresses high levels of a putative repellent that is the ligand for the Robo receptor. Growth cones that express high levels of Robo, such as ipsilaterally projecting growth cones from the outset or commissural growth cones once they cross the midline, are relatively immune to significant down-regulation by the normally low levels of midline Comm and thus are prevented from crossing the midline. Only abnormally high levels of Comm (using transgenes that drive overexpression) are sufficient to down-regulate this Robo expression to a level that allows these growth cones to cross the midline. In contrast, growth cones that normally express lower levels of Robo (i.e., those commissural growth cones that cross the midline in the presence of Comm) are highly sensitive to Comm, in that the normal low levels of Comm can further reduce their levels of Robo and thus allow them to cross the midline. In the absence of Comm, these growth cones can not cross the midline, due to their low levels of Robo; in the robo; comm double mutant they all freely cross.

Genetic Stocks. All robo alleles were isolated on chromosomes deficient for Fasciclin III as described in Seeger et al., 1993. The robo phenotype is independent of the absence of FasIII.

Protein Immunocytochemistry. Immunocytochemistry was performed as described by Patel (1994). For anti-Robo staining, MAb 13C9 was diluted 1:10 in PBS with 0.1% Tween-20, and the embryos were fixed and cracked so as to minimize exposure to methanol. The presence of triton and storage of embryos in methanol were both found to destroy the activity of MAb 13C9. For anti-Connectin staining with MAb C1.427, the embryos were fixed in 3.7% formaldehyde/PEM buffer (100 mM PIPES, 2 mM EGTA, 1 mM $MgSO_4$); C1.427 was diluted 1:10 in PBS with 0.1% Triton. The apterous-tau-lacZ embryos were hand devitellinized and dissected on poly-lysine coated slides and subsequently fixed for 20 minutes with 3.7% formaldehyde; rabbit anti-β-galactosidase (Cappell) was used at 1:10,000 and biotinylated anti-rabbit secondary was used at 1:1000 and enhanced with the Vectastain Elite ABC kit (Vector Laboratories).

Transformation of *Drosophila*, robo rescue and overexpression. The comm cDNA was inserted as a 1.7 kb XhoI-XbaI fragment into the XhoI and Xba sites of pUAST (Brand and Perrimon, 1993). Transformant lines were generated and mapped by standard procedures.

REFERENCES

Brand, A. H. and Perrimon, N. (1993) Development 118, 401–415.

Hidalgo, A., and Brand, A. H. (1997) Development 124, 3253–3262.

Kidd, T., Brose, K., Mitchell, K., Fetter, R., Tessier-Lavigne, M., Goodman, C. S., and Tear, G. (1997). Roundabout controls axon crossing of the CNS midline and defines a new subfamily of evolutionarily conserved guidance receptors. Cell, in review.

Klämbt, C., Jacobs, J. R., and Goodman, C. S. (1991) Cell 64, 801–815.

Lundgren, S. E., et al. (1995) Development 121, 1769–1773.

Mayer, U. and Nüsslein-Volhard, C. (1988) Genes Dev. 2, 1496–1511.

Meadows, L. A., et al. (1994) J. Cell Sci. 107, 321–328.

Nose, A., Mahajan, V. B., and Goodman, C. S. (1992) Cell 70, 553–567.

Patel, N. H. (1994) In "Methods in Cell Biology, Vol 44. *Drosophila melanogaster*: Practical Uses in Cell Biology" (L. S. B. Goldstein and E. Fyrberg, eds) Academic Press, New York.

Sambrook, J., Fritsch, E. F., and Maniatis, T. (1989). Molecular Cloning: A Laboratory Manual (Cold Spring Harbor, New York: Cold Spring Harbor Laboratory).

Seeger, M., Tear, G., Ferres-Marco, D. and Goodman C. S. (1993) Neuron 10, 409–426.

Tear G., et al. (1996) Neuron 16, 501–514.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of promoting axon outgrowth of a neuron determined to have expressed on its surface an amount of a natural human Robo and to be subject to an axon outgrowth repulsion mediated by the Robo, said method comprising the step of contacting the neuron with a natural Comm in an amount and under conditions sufficient to reduce the amount of Robo expressed on the neuron, wherein the Comm is provided to the neuron exogenously in a pharmaceutically acceptable composition, whereby the amount of Robo expressed on the surface is reduced, thereby reducing the outgrowth repulsion mediated by the Robo, and thereby promoting the axon outgrowth of the neuron.

2. A method according to claim 1, wherein the Robo consists of SEQ ID NO:8.

3. A method according to claim 1, wherein the Comm consists of SEQ ID NO:14.

4. A method according to claim 1, wherein the Comm consists of SEQ ID NO:14 and the Robo consists of SEQ ID NO:8.

5. A method according to claim 1, wherein the Comm is encoded by a natural sequence nucleic acid comprising SEQ ID NO:13.

6. A method according to claim 1, wherein the Comm is encoded by a natural sequence nucleic acid comprising SEQ ID NO:13 and the Robo consists of SEQ ID NO:8.

7. A method according to claim 1, wherein the neuron is in vitro.

8. A method according to claim 4, wherein the neuron is in vitro.

9. A method according to claim 5, wherein the neuron is in vitro.

10. A method according to claim 6, wherein the neuron is in vitro.

11. A method according to claim 1, wherein the neuron is in situ.

12. A method according to claim 4, wherein the neuron is in situ.

13. A method according to claim 5, wherein the neuron is in situ.

14. A method according to claim 6, wherein the neuron is in situ.

15. A method according to claim 1, wherein the neuron is in situ and the composition comprises fibers coated, embedded or derivatized with the Comm.

16. A method according to claim 4, wherein the neuron is in situ and the composition comprises fibers coated, embedded or derivatized with the Comm.

17. A method according to claim 5, wherein the neuron is in situ and the composition comprises fibers coated, embedded or derivatized with the Comm.

18. A method according to claim 6, wherein the neuron is in situ and the composition comprises fibers coated, embedded or derivatized with the Comm.

19. A method according to claim 1, wherein the neuron is in situ and the composition comprises a cell transformed to express the Comm.

20. A method according to claim 4, wherein the neuron is in situ and the composition comprises a cell transformed to express the Comm.

21. A method according to claim 5, wherein the neuron is in situ and the composition composes a cell transformed to express the Comm.

22. A method according to claim 6, wherein the neuron is in situ and the composition comprises a cell transformed to express the Comm.

* * * * *

SEQUENCE LISTING

<160> NUMBER OF SEQ ID NOS: 18

<210> SEQ ID NO 1
<211> LENGTH: 4188
<212> TYPE: DNA
<213> ORGANISM: Drosophila melanogaster

<400> SEQUENCE: 1

```
atgcatccca tgcatcccga aaaccacgcc atcgcccgga gcacgagcac cactaataac      60
ccatctcgca gtcggagcag caggatgtgg ctcctgcccg cctggctgct cctcgtcctg     120
gtggccagca atggcctgcc agcagtcaga ggccagtacc aatcgccacg tatcatcgag     180
catcccacgg atctggtcgt taagaagaat gaacccgcca cgctcaactg caaagtggag     240
ggcaagccgg aacccaccat tgagtggttt aaggatggcg aacccgtcag caccaacgaa     300
```

```
aagaaatcgc accgcgtcca gttcaaggac ggcgccctct tcttttacag gacaatgcaa      360
ggcaagaagg agcaggacgg cggagagtac tggtgcgtgg ccaagaaccg agtgggccag      420
gccgttagtc gccatgcctc cctccagata gctgttttgc gcgacgattt tcgcgtggag      480
cccaaagaca cgcgagtggc caaaggcgag acggctctgc tggagtgtgg gccgcccaaa      540
ggcattccag agccaacgct gatttggata aaggacggcg ttcccttgga cgacctgaaa      600
gccatgtcgt ttggcgccag ctcccgcgtt cgaattgtgg acggtggcaa cctgctgatc      660
agcaatgtgg agcccattga tgagggcaac tacaagtgca ttgcccagaa tctggtaggc      720
acccgcgaga gcagctatgc caagctgatt gtccaggtca aaccatactt tatgaaggag      780
cccaaggatc aggtgatgct ctacggccag acagccactt tccactgctc agtgggcggt      840
gatccgccgc cgaaagtgtt gtggaaaaag gaggagggca atattccggt gtccagagcg      900
cgaatccttc acgacgagaa aagtttagag atatccaaca taacgcccac cgatgagggc      960
acctatgtct gcgaggcaca caacaatgtc ggtcagatca cgctagggc ttctcttata     1020 gtccacgctc cgccgaactt tacgaaaaga cccagtaaca agaaagtggg actaaatggg     1080
gttgtccaac taccttgcat ggcctccgga aaccctccgc cgtctgtatt ctggaccaag     1140
gaaggagtat ccactcttat gttcccaaat agttcgcacg gaaggcagta tgtggctgcc     1200
gatgaaactc tgcagattac ggatgtgcgg caggaagacg aaggctacta tgtgtgttcc     1260
gctttcagtg tagtcgattc ctctacagta cgggttttcc tgcaagtcag ctcggtagac     1320
gagcgtccac ctccgattat tcaaatcgga cctgccaatc aaacactgcc caagggatca     1380
gttgctactt taccctgtcg ggccactgga aatcccagtc ccgtatcaa gtggttccac     1440 gatggacatg ccgtacaagc gggcaatcga tacagcatca tccaaggaag ctcactgaga     1500
gtcgatgacc ttcaactaag tgactctggt acctacacct gcactgcatc tggcgaacga     1560
ggagaaactt cctgggctgc cacactaacg gtggaaaaac ccggttctac atctcttcac     1620
cgggcagctg atcctagcac ttatcctgct cctccaggaa cacctaaagt cctgaatgtc     1680
agtcgcacca gcattagtct tcgttgggct aaaagccaag agaaacccgg agctgtgggc     1740
ccaatcattg gatacactgt agagtacttc agtccggatc tgcaaactgg ttggattgtg     1800
gctgcccatc gagtcggcga cactcaagtc actatctcgg gtctcactcc tggcacttcg     1860
tatgtgttcc tagttagagc tgagaatact cagggtattt ctgtgccttc cggcttatca     1920
aatgttatta aaaccattga ggcagatttc gatgcagctt ctgccaatga tttgtcagca     1980
gctcgaactt tgctgacagg aaagtcggtg gagctaatag atgcctcggc tatcaatgct     2040
agtgccgtta gacttgagtg gatgctccac gtgagcgctg atgagaaata cgtagagggc     2100
ctgcgcatac actataagga tgccagtgta ccatccgcac agtatcactc gatcactgtt     2160
atggatgcct ctgcagaatc gtttgtggtg ggaaaccttta agaagtacac caagtatgag     2220
ttcttcctaa cacccttttt tgagacaatt gaaggacagc ccagtaactc caagacagcc     2280
ctcacctatg aagatgttcc ctccgcacca ccggataaca ttcagattgg catgtacaac     2340
caaacagccg gttgggtgcg ttggactccg ccacccctccc agcaccacaa tggcaatttg     2400
tatggctaca agattgaggt cagcgccggt aacaccatga aggtgctggc caatatgact     2460
cttaatgcta ccaccacatc tgtgctccta aataacctaa ccaccggagc tgtgtacagc     2520
gtgaggttga actcctttac caaggcagga gatggacctt actccaaacc gatatcacta     2580
ttcatggacc ccacccatca tgtgcatccg ccacgggcac atccaagcgg cacccatgat     2640
gggcgacatg agggacagga tctcacgtat cataacaatg gcaacatacc acctggcgac     2700
```

-continued

```
attaatccca ccactcataa aaagaccact gactacctat ctggaccgtg gctaatggtg    2760
ctggtctgca tcgttcttct agtcctggtt atttcggcgg ctatttcgat ggtctacttc    2820
aagcgcaagc atcaaatgac caaggaattg ggtcacttaa gtgtggtcag tgacaacgaa    2880
ataaccgcat taaatatcaa tagcaaagag agcctttgga tagaccatca tcgtggatgg    2940
cgaactgccg atactgacaa agactcagga ttaagcgaat cgaagctact atcccacgtt    3000
aacagcagtc aatccaacta caataactcc gatggaggaa ccgattatgc agaagttgac    3060
acccgtaacc ttaccacctt ctacaattgt cgcaagagcc cgataatcc cacgccgtac     3120 gccaccacta tgatcattgg tacctcttcc agtgagacct gcaccaagac aacatctata    3180
agtgccgata aggactcggg aactcattcg ccctattctg acgcatttgc cggtcaggtg    3240
ccagcggttc ctgttgtcaa atccaactat cttcagtatc cggttgaacc gatcaactgg    3300
tcagagtttc tacccccgcc gccagaacac ccacctccgt cttctaccta tggatacgca    3360
caaggatctc ctgaatcttc gcggaagagc tccaaaagcg caggttccgg catttctaca    3420
aatcaaagca ttctgaacgc atccatacac agcagctcct cgggcggctt ttcagcttgg    3480
ggagtatcgc cccaatatgc tgtcgcctgt ccaccggaaa acgtttatag caatccgctg    3540
tcggcagtgg ctggcggcac ccagaaccgc tatcagataa cgcccacaaa ccaacatccg    3600
ccacagttac cggcctactt tgccaccacg ggtccaggag gagctgtacc acccaaccac    3660
ctgccatttg ccacacagcg tcatgcagcc agcgagtacc aggctggact gaatgcagcg    3720
cgatgtgccc aaagccgcgc ctgcaacagc tgcgatgcct tggccacacc ctcgcccatg    3780 caaccccac cgccagttcc cgtacccgag ggctggtacc aaccggtgca tcccaatagc     3840
cacccgatgc acccgacctc ctccaaccac cagatctacc agtgctcctc cgagtgctcg    3900
gatcactcga ggagctcgca gagtcacaag cggcagctgc agctcgagga gcacggcagc    3960
agtgccaaac aacgcggagg acaccaccgt cgacgagccc cggtggtgca gccgtgcatg    4020
gagagcgaga acgagaacat gctggcggag tacgagcagc gccagtacac cagcgattgc    4080
tgcaatagct cccgcgaggg cgacacctgc tcctgcagcg agggatcctg tctttacgcc    4140
gaggcgggcg agccggcgcc tcgtcaaatg actgctaaga cacctaa                  4188
```

<210> SEQ ID NO 2
<211> LENGTH: 1395
<212> TYPE: PRT
<213> ORGANISM: Drosophila melanogaster

<400> SEQUENCE: 2

```
Met His Pro Met His Pro Glu Asn His Ala Ile Ala Arg Ser Thr Ser
  1               5                  10                  15

Thr Thr Asn Asn Pro Ser Arg Ser Arg Ser Ser Arg Met Trp Leu Leu
             20                  25                  30

Pro Ala Trp Leu Leu Val Leu Val Ala Ser Asn Gly Leu Pro Ala
         35                  40                  45

Val Arg Gly Gln Tyr Gln Ser Pro Arg Ile Ile Glu His Pro Thr Asp
     50                  55                  60

Leu Val Val Lys Lys Asn Glu Pro Ala Thr Leu Asn Cys Lys Val Glu
 65                  70                  75                  80

Gly Lys Pro Glu Pro Thr Ile Glu Trp Phe Lys Asp Gly Glu Pro Val
                 85                  90                  95

Ser Thr Asn Glu Lys Lys Ser His Arg Val Gln Phe Lys Asp Gly Ala
            100                 105                 110
```

-continued

```
Leu Phe Phe Tyr Arg Thr Met Gln Gly Lys Lys Glu Gln Asp Gly Gly
            115                 120                 125

Glu Tyr Trp Cys Val Ala Lys Asn Arg Val Gly Gln Ala Val Ser Arg
130                 135                 140

His Ala Ser Leu Gln Ile Ala Val Leu Arg Asp Asp Phe Arg Val Glu
145                 150                 155                 160

Pro Lys Asp Thr Arg Val Ala Lys Gly Glu Thr Ala Leu Leu Glu Cys
                165                 170                 175

Gly Pro Pro Lys Gly Ile Pro Glu Pro Thr Leu Ile Trp Ile Lys Asp
                180                 185                 190

Gly Val Pro Leu Asp Asp Leu Lys Ala Met Ser Phe Gly Ala Ser Ser
            195                 200                 205

Arg Val Arg Ile Val Asp Gly Gly Asn Leu Leu Ile Ser Asn Val Glu
            210                 215                 220

Pro Ile Asp Glu Gly Asn Tyr Lys Cys Ile Ala Gln Asn Leu Val Gly
225                 230                 235                 240

Thr Arg Glu Ser Ser Tyr Ala Lys Leu Ile Val Gln Val Lys Pro Tyr
                245                 250                 255

Phe Met Lys Glu Pro Lys Asp Gln Val Met Leu Tyr Gly Gln Thr Ala
                260                 265                 270

Thr Phe His Cys Ser Val Gly Gly Asp Pro Pro Lys Val Leu Trp
            275                 280                 285

Lys Lys Glu Glu Gly Asn Ile Pro Val Ser Arg Ala Arg Ile Leu His
            290                 295                 300

Asp Glu Lys Ser Leu Glu Ile Ser Asn Ile Thr Pro Thr Asp Glu Gly
305                 310                 315                 320

Thr Tyr Val Cys Glu Ala His Asn Asn Val Gly Gln Ile Ser Ala Arg
                325                 330                 335

Ala Ser Leu Ile Val His Ala Pro Pro Asn Phe Thr Lys Arg Pro Ser
            340                 345                 350

Asn Lys Lys Val Gly Leu Asn Gly Val Val Gln Leu Pro Cys Met Ala
            355                 360                 365

Ser Gly Asn Pro Pro Ser Val Phe Trp Thr Lys Glu Gly Val Ser
370                 375                 380

Thr Leu Met Phe Pro Asn Ser Ser His Gly Arg Gln Tyr Val Ala Ala
385                 390                 395                 400

Asp Gly Thr Leu Gln Ile Thr Asp Val Arg Gln Glu Asp Glu Gly Tyr
                405                 410                 415

Tyr Val Cys Ser Ala Phe Ser Val Val Asp Ser Ser Thr Val Arg Val
                420                 425                 430

Phe Leu Gln Val Ser Ser Val Asp Glu Arg Pro Pro Ile Ile Gln
            435                 440                 445

Ile Gly Pro Ala Asn Gln Thr Leu Pro Lys Gly Ser Val Ala Thr Leu
            450                 455                 460

Pro Cys Arg Ala Thr Gly Asn Pro Ser Pro Arg Ile Lys Trp Phe His
465                 470                 475                 480

Asp Gly His Ala Val Gln Ala Gly Asn Arg Tyr Ser Ile Ile Gln Gly
                485                 490                 495

Ser Ser Leu Arg Val Asp Asp Leu Gln Leu Ser Asp Ser Gly Thr Tyr
                500                 505                 510

Thr Cys Thr Ala Ser Gly Glu Arg Gly Glu Thr Ser Trp Ala Ala Thr
            515                 520                 525
```

-continued

```
Leu Thr Val Glu Lys Pro Gly Ser Thr Ser Leu His Arg Ala Ala Asp
    530                 535                 540

Pro Ser Thr Tyr Pro Ala Pro Pro Gly Thr Pro Lys Val Leu Asn Val
545                 550                 555                 560

Ser Arg Thr Ser Ile Ser Leu Arg Trp Ala Lys Ser Gln Glu Lys Pro
                565                 570                 575

Gly Ala Val Gly Pro Ile Ile Gly Tyr Thr Val Glu Tyr Phe Ser Pro
                580                 585                 590

Asp Leu Gln Thr Gly Trp Ile Val Ala His Arg Val Gly Asp Thr
                595                 600                 605

Gln Val Thr Ile Ser Gly Leu Thr Pro Gly Thr Ser Tyr Val Phe Leu
    610                 615                 620

Val Arg Ala Glu Asn Thr Gln Gly Ile Ser Val Pro Ser Gly Leu Ser
625                 630                 635                 640

Asn Val Ile Lys Thr Ile Glu Ala Asp Phe Asp Ala Ala Ser Ala Asn
                645                 650                 655

Asp Leu Ser Ala Ala Arg Thr Leu Leu Thr Gly Lys Ser Val Glu Leu
                660                 665                 670

Ile Asp Ala Ser Ala Ile Asn Ala Ser Ala Val Arg Leu Glu Trp Met
                675                 680                 685

Leu His Val Ser Ala Asp Glu Lys Tyr Val Glu Gly Leu Arg Ile His
    690                 695                 700

Tyr Lys Asp Ala Ser Val Pro Ser Ala Gln Tyr His Ser Ile Thr Val
705                 710                 715                 720

Met Asp Ala Ser Ala Glu Ser Phe Val Val Gly Asn Leu Lys Lys Tyr
                725                 730                 735

Thr Lys Tyr Glu Phe Phe Leu Thr Pro Phe Phe Glu Thr Ile Glu Gly
                740                 745                 750

Gln Pro Ser Asn Ser Lys Thr Ala Leu Thr Tyr Glu Asp Val Pro Ser
                755                 760                 765

Ala Pro Pro Asp Asn Ile Gln Ile Gly Met Tyr Asn Gln Thr Ala Gly
    770                 775                 780

Trp Val Arg Trp Thr Pro Pro Ser Gln His Asn Gly Asn Leu
785                 790                 795                 800

Tyr Gly Tyr Lys Ile Glu Val Ser Ala Gly Asn Thr Met Lys Val Leu
                805                 810                 815

Ala Asn Met Thr Leu Asn Ala Thr Thr Thr Ser Val Leu Leu Asn Asn
                820                 825                 830

Leu Thr Thr Gly Ala Val Tyr Ser Val Arg Leu Asn Ser Phe Thr Lys
    835                 840                 845

Ala Gly Asp Gly Pro Tyr Ser Lys Pro Ile Ser Leu Phe Met Asp Pro
    850                 855                 860

Thr His His Val His Pro Pro Arg Ala His Pro Ser Gly Thr His Asp
865                 870                 875                 880

Gly Arg His Glu Gly Gln Asp Leu Thr Tyr His Asn Asn Gly Asn Ile
                885                 890                 895

Pro Pro Gly Asp Ile Asn Pro Thr Thr His Lys Lys Thr Thr Asp Tyr
                900                 905                 910

Leu Ser Gly Pro Trp Leu Met Val Leu Val Cys Ile Val Leu Leu Val
                915                 920                 925

Leu Val Ile Ser Ala Ala Ile Ser Met Val Tyr Phe Lys Arg Lys His
    930                 935                 940

Gln Met Thr Lys Glu Leu Gly His Leu Ser Val Val Ser Asp Asn Glu
```

-continued

```
            945                 950                 955                 960
Ile Thr Ala Leu Asn Ile Asn Ser Lys Glu Ser Leu Trp Ile Asp His
            965                 970                 975
His Arg Gly Trp Arg Thr Ala Asp Thr Asp Lys Asp Ser Gly Leu Ser
            980                 985                 990
Glu Ser Lys Leu Leu Ser His Val Asn Ser Ser Gln Ser Asn Tyr Asn
            995                1000                1005
Asn Ser Asp Gly Gly Thr Asp Tyr Ala Glu Val Asp Thr Arg Asn Leu
           1010                1015                1020
Thr Thr Phe Tyr Asn Cys Arg Lys Ser Pro Asp Asn Pro Thr Pro Tyr
1025                1030                1035                1040
Ala Thr Thr Met Ile Ile Gly Thr Ser Ser Glu Thr Cys Thr Lys
           1045                1050                1055
Thr Thr Ser Ile Ser Ala Asp Lys Asp Ser Gly Thr His Ser Pro Tyr
           1060                1065                1070
Ser Asp Ala Phe Ala Gly Gln Val Pro Ala Val Pro Val Val Lys Ser
           1075                1080                1085
Asn Tyr Leu Gln Tyr Pro Val Glu Pro Ile Asn Trp Ser Glu Phe Leu
           1090                1095                1100
Pro Pro Pro Pro Glu His Pro Pro Ser Ser Thr Tyr Gly Tyr Ala
1105                1110                1115                1120
Gln Gly Ser Pro Glu Ser Ser Arg Lys Ser Ser Lys Ser Ala Gly Ser
           1125                1130                1135
Gly Ile Ser Thr Asn Gln Ser Ile Leu Asn Ala Ser Ile His Ser Ser
           1140                1145                1150
Ser Ser Gly Gly Phe Ser Ala Trp Gly Val Ser Pro Gln Tyr Ala Val
           1155                1160                1165
Ala Cys Pro Pro Glu Asn Val Tyr Ser Asn Pro Leu Ser Ala Val Ala
           1170                1175                1180
Gly Gly Thr Gln Asn Arg Tyr Gln Ile Thr Pro Thr Asn Gln His Pro
1185                1190                1195                1200
Pro Gln Leu Pro Ala Tyr Phe Ala Thr Gly Pro Gly Gly Ala Val
           1205                1210                1215
Pro Pro Asn His Leu Pro Phe Ala Thr Gln Arg His Ala Ala Ser Glu
           1220                1225                1230
Tyr Gln Ala Gly Leu Asn Ala Ala Arg Cys Ala Gln Ser Arg Ala Cys
           1235                1240                1245
Asn Ser Cys Asp Ala Leu Ala Thr Pro Ser Pro Met Gln Pro Pro Pro
1250                1255                1260
Pro Val Pro Val Pro Glu Gly Trp Tyr Gln Pro Val His Pro Asn Ser
1265                1270                1275                1280
His Pro Met His Pro Thr Ser Ser Asn His Gln Ile Tyr Gln Cys Ser
           1285                1290                1295
Ser Glu Cys Ser Asp His Ser Arg Ser Ser Gln Ser His Lys Arg Gln
           1300                1305                1310
Leu Gln Leu Glu Glu His Gly Ser Ser Ala Lys Gln Arg Gly Gly His
           1315                1320                1325
His Arg Arg Arg Ala Pro Val Val Gln Pro Cys Met Glu Ser Glu Asn
           1330                1335                1340
Glu Asn Met Leu Ala Glu Tyr Glu Gln Arg Gln Tyr Thr Ser Asp Cys
1345                1350                1355                1360
Cys Asn Ser Ser Arg Glu Gly Asp Thr Cys Ser Cys Ser Glu Gly Ser
           1365                1370                1375
```

Cys Leu Tyr Ala Glu Ala Gly Glu Pro Ala Pro Arg Gln Met Thr Ala
        1380                1385                1390
Lys Asn Thr
    1395

<210> SEQ ID NO 3
<211> LENGTH: 4146
<212> TYPE: DNA
<213> ORGANISM: Drosophila melanogaster

<400> SEQUENCE: 3

| | | | | | | |
|---|---|---|---|---|---|---|
| ggtgaaaatc | cacgcatcat | cgagcatccc | atggacacga | cggtgccaaa | aaatgatcca | 60 |
| tttacgttta | attgccaggc | cgagggcaat | ccaacaccaa | ccattcaatg | gtttaaggac | 120 |
| ggtcgcgaac | tgaagacgga | tacgggttcg | catcgcataa | tgctgcccgc | cggggtcta | 180 |
| ttctttctca | aggttatcca | ctcacgtaga | gagagcgatg | cgggcactta | ctggtgcgag | 240 |
| gccaaaaacg | agtttggagt | ggcacggtcc | aggaatgcaa | cgttgcaagt | ggcagttctc | 300 |
| cgcgacgaat | ccgtttgga | gccggcaaat | acccgcgtgg | cccaaggcga | ggtggccctg | 360 |
| atggaatgcg | gtgcccccg | aggatctccg | gagccgcaaa | tctcgtggcg | caagaacggc | 420 |
| cagaccctga | atcttgtcgg | gaacaagcgg | attcgcattg | tcgacggtgg | caatctggcc | 480 |
| atccaggaag | cccgccaatc | ggacgacgga | cgctaccagt | gtgtggtcaa | gaatgtggtt | 540 |
| ggcacccggg | agtcggccac | cgcttttctt | aaagtgcatg | tacgtccatt | cctcatccga | 600 |
| ggaccccaga | atcagacggc | ggtggtgggc | agctcggtgt | tcttccagtg | ccgcatcgga | 660 |
| ggcgatcccc | tgcctgatgt | cctgtggcga | cgcactgcct | ccggcggcaa | tatgccactg | 720 |
| cgtaagtttt | cttggcttca | ttcagcttca | ggtcgtgtgc | acgtacttga | ggaccgcagt | 780 |
| ctgaagctgg | acgacgttac | tctggaggac | atgggcgagt | acacttgcga | ggcggacaat | 840 |
| gcggtgggcg | gcatcacggc | cactggcatc | ctcaccgttc | acgctccccc | caaatttgtg | 900 |
| atacgcccca | gaatcagct | ggtggagatc | ggtgatgaag | tgctgttcga | gtgccaagcg | 960 |
| aatggacatc | cccgaccaac | gctctactgg | tcggtggagg | gcaacagctc | cctgctgctc | 1020 |
| cccggctatc | gggatggccg | catggaagtg | accctgacgc | ccgaggggcg | ctcggtgctc | 1080 |
| tcgatagctc | gatttgcccg | tgaggattcc | ggaaaggtgg | tcacttgcaa | cgccctgaac | 1140 |
| gccgtgggca | gcgtcagcag | tcggactgtg | gtcagtgtgg | atacgcaatt | cgagctgcca | 1200 |
| ccgccgatta | tcgaacaggg | gcccgtgaat | caaacgttgc | ccgttaaatc | aattgtggtt | 1260 |
| ctgccatgcc | gaactctggg | cactccagtg | ccacaggtct | cttggtacct | ggatggcata | 1320 |
| cccatcgatg | tgcaggagca | cgagcggcgg | aatctttcgg | acgctggagc | cttaaccatt | 1380 |
| tcggatcttc | agcgccacga | ggatgaaggc | ttgtacacct | gcgtggccag | caatcgcaac | 1440 |
| ggaaaatcct | cttggagtgg | ttaccttcgt | ctggacaccc | cgacaaatcc | gaatatcaag | 1500 |
| ttcttcagag | ccccagaact | tccacctac | ccagggccgc | caggaaaacc | gcaaatggtg | 1560 |
| gagaagggcg | aaaattcggt | gactctcagc | tggacgagga | gcaacaaggt | gggcggctcc | 1620 |
| agtctggtgg | gctatgtaat | cgagatgttt | ggcaaaaacg | aaacggatgg | ctgggtggct | 1680 |
| gtgggcacta | gggtgcaaaa | taccacgttt | acccaaacgg | gtctgctgcc | gggtgtgaat | 1740 |
| tacttctttc | taattcgagc | cgagaactcc | catggcttat | cactgcccag | tccgatgtcg | 1800 |
| gaacccatta | cggtgggaac | gcgctacttc | aatagtggtc | tggatctgag | cgaggctcgt | 1860 |
| gccagtctgc | tgtccggaga | tgttgtggag | ctgagcaacg | ccagtgtggt | ggactccact | 1920 |

```
agcatgaaac tcacctggca gatcatcaat ggcaaatacg tcgagggctt ctatgtctat   1980
gcgagacagt tgccaaatcc aatagtcaac aatccggcgc ccgttactag caataccaat   2040
ccgctgctgg gctctacatc cacatccgca tccgcatccg cctcggcatc ggcattgatt   2100
tcgacaaagc caaatattgc agctgccggc aaacgtgatg gggagacaaa ccagagtgga   2160
ggaggagctc cgaccccact gaacaccaag tatcgcatgc taacgattct caatggcggt   2220
ggcgcctcat cctgcaccat caccgggctc gtccagtaca cgctgtatga atttttcatc   2280
gtgccatttt acaaatccgt cgagggcaag ccgtcgaatt cgcgcatcgc tcgcacccct   2340
gaagatgttc cctctgaggc accatatgga atggaggctc tgctgttgaa ctcctccgcg   2400
gtcttcctca aatggaaggc accagaactc aaggatcggc atggtgttct cttgaactat   2460
catgttatag tccgaggtat tgacactgcc cacaatttct cacgcatttt gacaaatgtc   2520
accatcgatg ccgcttcgcc tactctggtt ttggccaatc tcaccgaagg cgtcatgtac   2580
accgtgggcg tggcggccgg aaataacgct ggagttggtc cttattgtgt cccagctact   2640
ttgcgtttgg atcccatcac aaagcgactc gatccgttca tcaatcagcg ggaccatgtt   2700
aacgatgtgc tgacgcagcc ctggttcata atactcctgg gcgccatcct ggccgttctt   2760
atgctgtcct ttggcgcaat ggtctttgtg aagcgcaagc acatgatgat gaagcagtcg   2820
gccctaaata caatgcgtgg caatcacacg agcgacgtgc tcaaaatgcc gagtctatcg   2880
gcgcgcaatg gaaacggcta ctggctggac tcctccaccg gcggaatggt gtggcgtccc   2940
tcgcccggcg gcgactcgct ggagatgcaa aaggatcaca tcgccgacta tgcgccggtc   3000
tgcggtgccc ccggttctcc ggccggcggt ggcacctctt ccggtggatc cggtggcgcg   3060
ggcagcggtg ccagcggcgg cgatgacatt catggaggac acggcagcga acgcaatcag   3120
cagcggtacg tgggcgagta ctccaacata ccgaccgact atgcagaggt gtccagtttt   3180
ggcaaggcac ccagcgagta tggtcggcat ggcaacgcct ccccggcccc ttatgccacc   3240
tcttcgatcc tgagtcccca ccagcagcaa cagcagcagc agccgcgtta tcaacagcga   3300
ccagtgcccg gctatgggct ccagcgccca atgcacccac actaccagca gcagcagcat   3360
cagcagcaac aggcgcagca gacgcaccag caacaccagg ctctccagca gcaccagcaa   3420
ctgccaccca gcaacatcta ccagcagatg tccaccacca gcgagatata ccccacgaac   3480
acgggtcctt cgcgctctgt ctactctgag cagtattact accccaagga caagcagaga   3540
cacatccaca tcaccgagaa caagctgagc aactgccaca cctatgaggc ggctcctggc   3600
gccaagcagt cctcgccgat atcctcgcag ttcgccagcg tgaggcggca gcagctgccg   3660
cccaactgca gcatcggcag ggaaagtgcc cgcttcaagg tgctaaacac ggatcagggc   3720
aagaaccagc agaatctcct ggatctcgac ggctcctcga tgtgctacaa cggtctggca   3780
gactcgggct gcggtggatc tccctccccg atggccatgc tgatgtcgca cgaggacgag   3840
cacgcgctgt accacggc ggatgggat ctggacgaca tggaacgact gtacgtcaag   3900
gtggacgagc agcagcctcc acagcagcag cagcagctga ttcccctggt cccacagcat   3960
ccggcggaag gtcacctgca gtcctggcgg aatcagagca cgcggagcag tcggaagaac   4020
ggccaggaat gcatcaagga acccagcgag ttgatctacg ctccgggaag cgtggccagc   4080
gaacggagcc tcctcagcaa ctcgggtagc ggcaccagca gccagccagc tggccacaat   4140
gtctga                                                              4146
```

<210> SEQ ID NO 4
<211> LENGTH: 1381

```
<212> TYPE: PRT
<213> ORGANISM: Drosophila melanogaster

<400> SEQUENCE: 4

Gly Glu Asn Pro Arg Ile Ile Glu His Pro Met Asp Thr Thr Val Pro
  1               5                  10                  15

Lys Asn Asp Pro Phe Thr Phe Asn Cys Gln Ala Glu Gly Asn Pro Thr
                 20                  25                  30

Pro Thr Ile Gln Trp Phe Lys Asp Gly Arg Glu Leu Lys Thr Asp Thr
             35                  40                  45

Gly Ser His Arg Ile Met Leu Pro Ala Gly Gly Leu Phe Phe Leu Lys
         50                  55                  60

Val Ile His Ser Arg Arg Glu Ser Asp Ala Gly Thr Tyr Trp Cys Glu
 65                  70                  75                  80

Ala Lys Asn Glu Phe Gly Val Ala Arg Ser Arg Asn Ala Thr Leu Gln
                 85                  90                  95

Val Ala Val Leu Arg Asp Glu Phe Arg Leu Glu Pro Ala Asn Thr Arg
            100                 105                 110

Val Ala Gln Gly Glu Val Ala Leu Met Glu Cys Gly Ala Pro Arg Gly
            115                 120                 125

Ser Pro Glu Pro Gln Ile Ser Trp Arg Lys Asn Gly Gln Thr Leu Asn
130                 135                 140

Leu Val Gly Asn Lys Arg Ile Arg Ile Val Asp Gly Gly Asn Leu Ala
145                 150                 155                 160

Ile Gln Glu Ala Arg Gln Ser Asp Asp Gly Arg Tyr Gln Cys Val Val
                165                 170                 175

Lys Asn Val Val Gly Thr Arg Glu Ser Ala Thr Ala Phe Leu Lys Val
            180                 185                 190

His Val Arg Pro Phe Leu Ile Arg Gly Pro Gln Asn Gln Thr Ala Val
            195                 200                 205

Val Gly Ser Ser Val Val Phe Gln Cys Arg Ile Gly Gly Asp Pro Leu
            210                 215                 220

Pro Asp Val Leu Trp Arg Arg Thr Ala Ser Gly Gly Asn Met Pro Leu
225                 230                 235                 240

Arg Lys Phe Ser Trp Leu His Ser Ala Ser Gly Arg Val His Val Leu
                245                 250                 255

Glu Asp Arg Ser Leu Lys Leu Asp Asp Val Thr Leu Glu Asp Met Gly
            260                 265                 270

Glu Tyr Thr Cys Glu Ala Asp Asn Ala Val Gly Gly Ile Thr Ala Thr
            275                 280                 285

Gly Ile Leu Thr Val His Ala Pro Pro Lys Phe Val Ile Arg Pro Lys
            290                 295                 300

Asn Gln Leu Val Glu Ile Gly Asp Glu Val Leu Phe Glu Cys Gln Ala
305                 310                 315                 320

Asn Gly His Pro Arg Pro Thr Leu Tyr Trp Ser Val Glu Gly Asn Ser
                325                 330                 335

Ser Leu Leu Leu Pro Gly Tyr Arg Asp Gly Arg Met Glu Val Thr Leu
            340                 345                 350

Thr Pro Glu Gly Arg Ser Val Leu Ser Ile Ala Arg Phe Ala Arg Glu
            355                 360                 365

Asp Ser Gly Lys Val Val Thr Cys Asn Ala Leu Asn Ala Val Gly Ser
            370                 375                 380

Val Ser Ser Arg Thr Val Val Ser Val Asp Thr Gln Phe Glu Leu Pro
385                 390                 395                 400
```

-continued

```
Pro Pro Ile Ile Glu Gln Gly Pro Val Asn Gln Thr Leu Pro Val Lys
            405                 410                 415

Ser Ile Val Val Leu Pro Cys Arg Thr Leu Gly Thr Pro Val Pro Gln
        420                 425                 430

Val Ser Trp Tyr Leu Asp Gly Ile Pro Ile Asp Val Gln Glu His Glu
    435                 440                 445

Arg Arg Asn Leu Ser Asp Ala Gly Ala Leu Thr Ile Ser Asp Leu Gln
450                 455                 460

Arg His Glu Asp Glu Gly Leu Tyr Thr Cys Val Ala Ser Asn Arg Asn
465                 470                 475                 480

Gly Lys Ser Ser Trp Ser Gly Tyr Leu Arg Leu Asp Thr Pro Thr Asn
                485                 490                 495

Pro Asn Ile Lys Phe Phe Arg Ala Pro Glu Leu Ser Thr Tyr Pro Gly
            500                 505                 510

Pro Pro Gly Lys Pro Gln Met Val Glu Lys Gly Glu Asn Ser Val Thr
        515                 520                 525

Leu Ser Trp Thr Arg Ser Asn Lys Val Gly Gly Ser Ser Leu Val Gly
    530                 535                 540

Tyr Val Ile Glu Met Phe Gly Lys Asn Glu Thr Asp Gly Trp Val Ala
545                 550                 555                 560

Val Gly Thr Arg Val Gln Asn Thr Thr Phe Thr Gln Thr Gly Leu Leu
                565                 570                 575

Pro Gly Val Asn Tyr Phe Phe Leu Ile Arg Ala Glu Asn Ser His Gly
            580                 585                 590

Leu Ser Leu Pro Ser Pro Met Ser Glu Pro Ile Thr Val Gly Thr Arg
        595                 600                 605

Tyr Phe Asn Ser Gly Leu Asp Leu Ser Glu Ala Arg Ala Ser Leu Leu
    610                 615                 620

Ser Gly Asp Val Val Glu Leu Ser Asn Ala Ser Val Val Asp Ser Thr
625                 630                 635                 640

Ser Met Lys Leu Thr Trp Gln Ile Ile Asn Gly Lys Tyr Val Glu Gly
                645                 650                 655

Phe Tyr Val Tyr Ala Arg Gln Leu Pro Asn Pro Ile Val Asn Asn Pro
            660                 665                 670

Ala Pro Val Thr Ser Asn Thr Asn Pro Leu Leu Gly Ser Thr Ser Thr
        675                 680                 685

Ser Ala Ser Ala Ser Ala Ser Ala Leu Ile Ser Thr Lys Pro
    690                 695                 700               Pro

Asn Ile Ala Ala Ala Gly Lys Arg Asp Gly Glu Thr Asn Gln Ser Gly
705                 710                 715                 720

Gly Gly Ala Pro Thr Pro Leu Asn Thr Lys Tyr Arg Met Leu Thr Ile
                725                 730                 735

Leu Asn Gly Gly Gly Ala Ser Ser Cys Thr Ile Thr Gly Leu Val Gln
            740                 745                 750

Tyr Thr Leu Tyr Glu Phe Phe Ile Val Pro Phe Tyr Lys Ser Val Glu
        755                 760                 765

Gly Lys Pro Ser Asn Ser Arg Ile Ala Arg Thr Leu Glu Asp Val Pro
    770                 775                 780

Ser Glu Ala Pro Tyr Gly Met Glu Ala Leu Leu Leu Asn Ser Ser Ala
785                 790                 795                 800

Val Phe Leu Lys Trp Lys Ala Pro Glu Leu Lys Asp Arg His Gly Val
                805                 810                 815
```

-continued

```
Leu Leu Asn Tyr His Val Ile Val Arg Gly Ile Asp Thr Ala His Asn
            820                 825                 830
Phe Ser Arg Ile Leu Thr Asn Val Thr Ile Asp Ala Ala Ser Pro Thr
        835                 840                 845
Leu Val Leu Ala Asn Leu Thr Glu Gly Val Met Tyr Thr Val Gly Val
    850                 855                 860
Ala Ala Gly Asn Asn Ala Gly Val Gly Pro Tyr Cys Val Pro Ala Thr
865                 870                 875                 880
Leu Arg Leu Asp Pro Ile Thr Lys Arg Leu Asp Pro Phe Ile Asn Gln
                885                 890                 895
Arg Asp His Val Asn Asp Val Leu Thr Gln Pro Trp Phe Ile Ile Leu
            900                 905                 910
Leu Gly Ala Ile Leu Ala Val Leu Met Leu Ser Phe Gly Ala Met Val
        915                 920                 925
Phe Val Lys Arg Lys His Met Met Lys Gln Ser Ala Leu Asn Thr
    930                 935                 940
Met Arg Gly Asn His Thr Ser Asp Val Leu Lys Met Pro Ser Leu Ser
945                 950                 955                 960
Ala Arg Asn Gly Asn Gly Tyr Trp Leu Asp Ser Ser Thr Gly Gly Met
                965                 970                 975
Val Trp Arg Pro Ser Pro Gly Gly Asp Ser Leu Glu Met Gln Lys Asp
            980                 985                 990
His Ile Ala Asp Tyr Ala Pro Val Cys Gly Ala Pro Gly Ser Pro Ala
        995                 1000                1005
Gly Gly Gly Thr Ser Ser Gly Gly Ser Gly Ala Gly Ser Gly Ala
    1010                1015                1020
Ser Gly Gly Asp Asp Ile His Gly Gly His Gly Ser Glu Arg Asn Gln
1025                1030                1035                1040
Gln Arg Tyr Val Gly Glu Tyr Ser Asn Ile Pro Thr Asp Tyr Ala Glu
                1045                1050                1055
Val Ser Ser Phe Gly Lys Ala Pro Ser Glu Tyr Gly Arg His Gly Asn
            1060                1065                1070
Ala Ser Pro Ala Pro Tyr Ala Thr Ser Ser Ile Leu Ser Pro His Gln
        1075                1080                1085
Gln Gln Gln Gln Gln Gln Pro Arg Tyr Gln Gln Arg Pro Val Pro Gly
    1090                1095                1100
Tyr Gly Leu Gln Arg Pro Met His Pro His Tyr Gln Gln Gln Gln His
1105                1110                1115                1120
Gln Gln Gln Gln Ala Gln Gln Thr His Gln Gln His Gln Ala Leu Gln
                1125                1130                1135
Gln His Gln Gln Leu Pro Pro Ser Asn Ile Tyr Gln Gln Met Ser Thr
            1140                1145                1150
Thr Ser Glu Ile Tyr Pro Thr Asn Thr Gly Pro Ser Arg Ser Val Tyr
        1155                1160                1165
Ser Glu Gln Tyr Tyr Tyr Pro Lys Asp Lys Gln Arg His Ile His Ile
    1170                1175                1180
Thr Glu Asn Lys Leu Ser Asn Cys His Thr Tyr Glu Ala Ala Pro Gly
1185                1190                1195                1200
Ala Lys Gln Ser Ser Pro Ile Ser Ser Gln Phe Ala Ser Val Arg Arg
                1205                1210                1215
Gln Gln Leu Pro Pro Asn Cys Ser Ile Gly Arg Glu Ser Ala Arg Phe
            1220                1225                1230
Lys Val Leu Asn Thr Asp Gln Gly Lys Asn Gln Gln Asn Leu Leu Asp
```

-continued

```
                1235                1240                1245
Leu Asp Gly Ser Ser Met Cys Tyr Asn Gly Leu Ala Asp Ser Gly Cys
    1250                1255                1260
Gly Gly Ser Pro Ser Pro Met Ala Met Leu Met Ser His Glu Asp Glu
1265                1270                1275                1280
His Ala Leu Tyr His Thr Ala Asp Gly Asp Leu Asp Asp Met Glu Arg
                1285                1290                1295
Leu Tyr Val Lys Val Asp Glu Gln Gln Pro Pro Gln Gln Gln Gln Gln
            1300                1305                1310
Leu Ile Pro Leu Val Pro Gln His Pro Ala Glu Gly His Leu Gln Ser
        1315                1320                1325
Trp Arg Asn Gln Ser Thr Arg Ser Ser Arg Lys Asn Gly Gln Glu Cys
    1330                1335                1340
Ile Lys Glu Pro Ser Glu Leu Ile Tyr Ala Pro Gly Ser Val Ala Ser
1345                1350                1355                1360
Glu Arg Ser Leu Leu Ser Asn Ser Gly Ser Gly Thr Ser Ser Gln Pro
                1365                1370                1375
Ala Gly His Asn Val
        1380

<210> SEQ ID NO 5
<211> LENGTH: 3894
<212> TYPE: DNA
<213> ORGANISM: Caenorhabditis elegans

<400> SEQUENCE: 5
atgtactatc taggttttta ccacactcac acacacacac acacatacat aaattttgat    60
aaaattccta atgcctcaaa tctcgctccc gtgataatcg aacatcccat cgatgtggtg   120
gtatctaggg gatcgccagc aaccctcaac tgtggtgcaa agccatctac cgccaaaatc   180
acatggtaca aggatggaca gcccgtaatc acgaataagg agcaagtgaa cagccaccgg   240
attgttctcg acacgggatc cctgtttctt ctgaaagtga atagtggaaa aacggaaaa    300
gacagcgatg cgggagcgta ctattgtgtg ccagcaacg agcacggaga agtgaagtcg    360
aacgaaggat cgttaaaatt ggcgatgctt cgcgaagact ttcgagttcg gccaagaaca    420
gttcaggctc ttggtggaga gatggccgtt ctggaatgca gtccgccacg tggattcccg    480
gagccggttg tgagctggcg gaaagacgac aaagagctcc gaattcaaga catgccacga    540
tacactctac actctgacgg aaacctcatc attgatccgg tcgatcgaag cgattctggt    600
acttatcagt gtgttgccaa caacatggtc ggagaacggg tgtccaatcc cgcaagattg    660
agtgtctttg agaaaccaaa gtttgagcaa gaacccaagg acatgacggt cgacgtcgga    720
gccgcagtgc tgtttgattg tcgtgtgact ggagatcctc aaccacaaat tacgtggaaa    780
cgcaaaaatg agccgatgcc agttacacgt gcatacattg ccaaggataa tcggggggttg    840
agaatcgaaa gagttcaacc atcagacgaa ggtgaatacg tttgctatgc acgaaatcca    900
gcgggaactc ttgaagcatc tgcacatctt cgtgtccagg cacctccatc cttccagaca    960
aaaccagcag accagtcagt tccagctgga ggcacggcaa cttttgaatg caccttggtc   1020
ggtcaaccga gtcccgccta tttttggagc aaggaaggcc aacaggatct tcttttccca   1080
agttatgtgt ccgctgatgg tagaacgaaa gtttcaccaa ctggaacatt gacaattgag   1140
gaagttcgtc aagttgatga gggagcttat gtgtgcgctg gaatgaactc ggcaggaagc   1200
tcgttgagca aggcagcttt gaaagcaaca tttgaaacca aggccgtgt ccaaaaaaaa   1260
```

```
aagagcaaaa tgggcaaaca gaaacaaaaa aatgttcaat caattatcaa atatttaatt    1320
tcagccgtga ccggaaacac acccgccaaa ccaccaccaa caatcgagca tggtcatcaa    1380
aatcagaccc ttatggttgg atcatcagcc atccttccat gtcaggctag cggaaaacca    1440
actccaggaa tatcatggct cagggatggg ctacctattg acattacaga tagtcgtatc    1500
agtcaacatt caacgggaag tctacatatt gccgatttaa agaaacctga caccggagtt    1560
tacacttgca ttgcgaagaa cgaggatgga gagtcaacat ggtcggcatc tctgactgtt    1620
gaagatcaca ctagcaatgc acaatttgtt cggatgccgg atccatcgaa cttcccgtct    1680
tctccaacgc aacccattat tgtcaatgtc actgataccg aagtagagct ccactggaat    1740
gctccctcca catctggcgc aggaccaatc actggttata tcattcagta ctacagtcca    1800
gacctcggac agacgtggtt taacattcca gactacgtgg catctactga atatagaata    1860
aagggtctga aaccatctca ctcgtatatg tttgtgattc gagcagaaaa tgagaaggt    1920 attggaacgc cgagtgtgtc gtcggctctc gttaccacta gcaagccagc agctcaagtt    1980
gcgctttctg acaagaacaa aatggacatg ccatcgctg agaagagact cacttcggaa    2040
caactcataa aactcgagga agtgaagact attaattcta cggccgttcg tttgttctgg    2100
aagaagagga aacttgaaga gctgattgat ggttactaca tcaagtggag agggcctcca    2160
agaaccaatg ataatcaata cgtgaatgtg accagcccta gcaccgaaaa ctatgttgtt    2220
tcaaatttaa tgccattcac caactatgag tttttcgtga ttccttatca ttccggagtt    2280
catagtattc atggagcacc gagtaattcc atggacgtgt tgaccgccga agctccacct    2340
tcattgccac cagaggatgt gcgaatccgt atgctcaacc tgaccactct tcgtatctct    2400
tggaaagcac caaaagccga cggcatcaac ggaattctca aaggattcca aattgttatt    2460
gttggtcaag cgcccaacaa caatcggaac atcactacaa acgagagagc tgccagtgtt    2520
actctgttcc atttagtgac tggaatgacg tataaaattc gtgtagcggc tagaagcaat    2580
ggtggagttg gagtctcaca tggaacgagt gaagtcatca tgaatcaaga cacgctggaa    2640
aaacaccttg ctgctcaaca agaaaacgaa tcattttttgt atgggctgat caataaatct    2700
catgttcctg tgattgtcat tgttgcaatt ctgattattt tcgtagtcat cattatagcc    2760
tattgttact ggaggaatag cagaaacagt gatggaaagg atcgaagttt tataaagatc    2820
aatgatggaa gtgttcatat ggcttcgaat aatctttggg atgttgcaca aaatccgaat    2880
cagaatccaa tgtacaacac tgctggaaga atgactatga acaatagaaa tggccaggct    2940
ctctattcgc tgacaccaaa tgcgcaagac ttttcaaca attgtgatga ctacagtgga    3000
acgatgcaca gaccaggatc cgagcatcac tatcattatg ctcaactgac tggcggaccct    3060 ggtaatgcga tgtctacttt ttatggaaac caatatcacg atgatccatc tccatatgcc    3120
accacaacac tggtcctgtc gaaccaacaa ccagcttggc tcaatgacaa aatgcttcgc    3180
gcgccagcaa tgccaacaaa tcccgtgcca ccagagccac cggcgcgata tgcagatcat    3240
accgctggaa gacgatctcg atcgagccgt gcatccgatg ggagaggaac tctgaatggc    3300
ggactccatc accggactag cggaagtcaa cggtcggata gtccacctca cacagatgtg    3360
agctatgttc agcttcactc atccgatgga actggtagta gtaaggaaag aactggggag    3420
cggagaaaca caccgaataa gactctgatg gactttattc cgccaccacc ttccaatcca    3480
ccaccacctg gagggcacgt ttatgacaca gcaactaggc gtcagttgaa tcgtggaagt    3540
actccacgag aagacaccta cgattcggtc agtgacggag cttttgctcg ggttgatgtg    3600
aatgcaaggc caacgagtcg gaatcggaat ttgggaggaa ggccgctgaa agggaaacga    3660
```

```
gacgacgata gtcagcggtc ttcgttgatg atggacgatg atggtggatc ttctgaagct   3720
gacggggaga actctgaagg agacgttccg cgtggaggtg ttagaaaagc agttcctcga   3780
atgggtatct ctgcaagtac gctggctcat agttgttacg ggacaaacgg cactgctcaa   3840
cgattccggt caattccacg taacaatgga atcgtcacac aagaacaaac ttga         3894
```

<210> SEQ ID NO 6
<211> LENGTH: 1297
<212> TYPE: PRT
<213> ORGANISM: Caenorhabditis elegans

<400> SEQUENCE: 6

```
Met Tyr Tyr Leu Gly Phe Tyr His Thr His Thr His Thr His Thr Tyr
  1               5                  10                  15

Ile Asn Phe Asp Lys Ile Pro Asn Ala Ser Asn Leu Ala Pro Val Ile
             20                  25                  30

Ile Glu His Pro Ile Asp Val Val Ser Arg Gly Ser Pro Ala Thr
         35                  40                  45

Leu Asn Cys Gly Ala Lys Pro Ser Thr Ala Lys Ile Thr Trp Tyr Lys
 50                  55                  60

Asp Gly Gln Pro Val Ile Thr Asn Lys Glu Gln Val Asn Ser His Arg
 65                  70                  75                  80

Ile Val Leu Asp Thr Gly Ser Leu Phe Leu Leu Lys Val Asn Ser Gly
                 85                  90                  95

Lys Asn Gly Lys Asp Ser Asp Ala Gly Ala Tyr Tyr Cys Val Ala Ser
            100                 105                 110

Asn Glu His Gly Glu Val Lys Ser Asn Glu Gly Ser Leu Lys Leu Ala
        115                 120                 125

Met Leu Arg Glu Asp Phe Arg Val Arg Pro Arg Thr Val Gln Ala Leu
130                 135                 140

Gly Gly Glu Met Ala Val Leu Glu Cys Ser Pro Arg Gly Phe Pro
145                 150                 155                 160

Glu Pro Val Val Ser Trp Arg Lys Asp Lys Glu Leu Arg Ile Gln
                165                 170                 175

Asp Met Pro Arg Tyr Thr Leu His Ser Asp Gly Asn Leu Ile Ile Asp
            180                 185                 190

Pro Val Asp Arg Ser Asp Ser Gly Thr Tyr Gln Cys Val Ala Asn Asn
        195                 200                 205

Met Val Gly Glu Arg Val Ser Asn Pro Ala Arg Leu Ser Val Phe Glu
    210                 215                 220

Lys Pro Lys Phe Glu Gln Glu Pro Lys Asp Met Thr Val Asp Val Gly
225                 230                 235                 240

Ala Ala Val Leu Phe Asp Cys Arg Val Thr Gly Asp Pro Gln Pro Gln
                245                 250                 255

Ile Thr Trp Lys Arg Lys Asn Glu Pro Met Pro Val Thr Arg Ala Tyr
            260                 265                 270

Ile Ala Lys Asp Asn Arg Gly Leu Arg Ile Glu Arg Val Gln Pro Ser
        275                 280                 285

Asp Glu Gly Glu Tyr Val Cys Tyr Ala Arg Asn Pro Ala Gly Thr Leu
    290                 295                 300

Glu Ala Ser Ala His Leu Arg Val Gln Ala Pro Ser Phe Gln Thr
305                 310                 315                 320

Lys Pro Ala Asp Gln Ser Val Pro Ala Gly Gly Thr Ala Thr Phe Glu
                325                 330                 335
```

-continued

```
Cys Thr Leu Val Gly Gln Pro Ser Pro Ala Tyr Phe Trp Ser Lys Glu
            340                 345                 350
Gly Gln Gln Asp Leu Leu Phe Pro Ser Tyr Val Ser Ala Asp Gly Arg
        355                 360                 365
Thr Lys Val Ser Pro Thr Gly Thr Leu Thr Ile Glu Glu Val Arg Gln
    370                 375                 380
Val Asp Glu Gly Ala Tyr Val Cys Ala Gly Met Asn Ser Ala Gly Ser
385                 390                 395                 400
Ser Leu Ser Lys Ala Ala Leu Lys Ala Thr Phe Glu Thr Lys Gly Arg
                405                 410                 415
Val Gln Lys Lys Lys Ser Lys Met Gly Lys Gln Lys Gln Lys Asn Val
            420                 425                 430
Gln Ser Ile Ile Lys Tyr Leu Ile Ser Ala Val Thr Gly Asn Thr Pro
        435                 440                 445
Ala Lys Pro Pro Pro Thr Ile Glu His Gly His Gln Asn Gln Thr Leu
    450                 455                 460
Met Val Gly Ser Ser Ala Ile Leu Pro Cys Gln Ala Ser Gly Lys Pro
465                 470                 475                 480
Thr Pro Gly Ile Ser Trp Leu Arg Asp Gly Leu Pro Ile Asp Ile Thr
                485                 490                 495
Asp Ser Arg Ile Ser Gln His Ser Thr Gly Ser Leu His Ile Ala Asp
            500                 505                 510
Leu Lys Lys Pro Asp Thr Gly Val Tyr Thr Cys Ile Ala Lys Asn Glu
        515                 520                 525
Asp Gly Glu Ser Thr Trp Ser Ala Ser Leu Thr Val Glu Asp His Thr
    530                 535                 540
Ser Asn Ala Gln Phe Val Arg Met Pro Asp Pro Ser Asn Phe Pro Ser
545                 550                 555                 560
Ser Pro Thr Gln Pro Ile Ile Val Asn Val Thr Asp Thr Glu Val Glu
                565                 570                 575
Leu His Trp Asn Ala Pro Ser Thr Ser Gly Ala Gly Pro Ile Thr Gly
            580                 585                 590
Tyr Ile Ile Gln Tyr Tyr Ser Pro Asp Leu Gly Gln Thr Trp Phe Asn
        595                 600                 605
Ile Pro Asp Tyr Val Ala Ser Thr Glu Tyr Arg Ile Lys Gly Leu Lys
    610                 615                 620
Pro Ser His Ser Tyr Met Phe Val Ile Arg Ala Glu Asn Glu Lys Gly
625                 630                 635                 640
Ile Gly Thr Pro Ser Val Ser Ser Ala Leu Val Thr Thr Ser Lys Pro
                645                 650                 655
Ala Ala Gln Val Ala Leu Ser Asp Lys Asn Lys Met Asp Met Ala Ile
            660                 665                 670
Ala Glu Lys Arg Leu Thr Ser Glu Gln Leu Ile Lys Leu Glu Glu Val
        675                 680                 685
Lys Thr Ile Asn Ser Thr Ala Val Arg Leu Phe Trp Lys Lys Arg Lys
    690                 695                 700
Leu Glu Glu Leu Ile Asp Gly Tyr Tyr Ile Lys Trp Arg Gly Pro Pro
705                 710                 715                 720
Arg Thr Asn Asp Asn Gln Tyr Val Asn Val Thr Ser Pro Ser Thr Glu
                725                 730                 735
Asn Tyr Val Val Ser Asn Leu Met Pro Phe Thr Asn Tyr Glu Phe Phe
            740                 745                 750
```

-continued

```
Val Ile Pro Tyr His Ser Gly Val His Ser Ile His Gly Ala Pro Ser
        755                 760                 765
Asn Ser Met Asp Val Leu Thr Ala Glu Ala Pro Pro Ser Leu Pro Pro
        770                 775                 780
Glu Asp Val Arg Ile Arg Met Leu Asn Leu Thr Thr Leu Arg Ile Ser
785                 790                 795                 800
Trp Lys Ala Pro Lys Ala Asp Gly Ile Asn Gly Ile Leu Lys Gly Phe
                    805                 810                 815
Gln Ile Val Ile Val Gly Gln Ala Pro Asn Asn Arg Asn Ile Thr
                    820                 825                 830
Thr Asn Glu Arg Ala Ala Ser Val Thr Leu Phe His Leu Val Thr Gly
                    835                 840                 845
Met Thr Tyr Lys Ile Arg Val Ala Ala Arg Ser Asn Gly Gly Val Gly
        850                 855                 860
Val Ser His Gly Thr Ser Glu Val Ile Met Asn Gln Asp Thr Leu Glu
865                 870                 875                 880
Lys His Leu Ala Ala Gln Gln Glu Asn Glu Ser Phe Leu Tyr Gly Leu
                    885                 890                 895
Ile Asn Lys Ser His Val Pro Val Ile Val Ala Ile Leu Ile
                    900                 905                 910
Ile Phe Val Val Ile Ile Ala Tyr Cys Tyr Trp Arg Asn Ser Arg
        915                 920                 925
Asn Ser Asp Gly Lys Asp Arg Ser Phe Ile Lys Ile Asn Asp Gly Ser
        930                 935                 940
Val His Met Ala Ser Asn Asn Leu Trp Asp Val Ala Gln Asn Pro Asn
945                 950                 955                 960
Gln Asn Pro Met Tyr Asn Thr Ala Gly Arg Met Thr Met Asn Asn Arg
                    965                 970                 975
Asn Gly Gln Ala Leu Tyr Ser Leu Thr Pro Asn Ala Gln Asp Phe Phe
                    980                 985                 990
Asn Asn Cys Asp Asp Tyr Ser Gly Thr Met His Arg Pro Gly Ser Glu
                    995                 1000                1005
His His Tyr His Tyr Ala Gln Leu Thr Gly Gly Pro Gly Asn Ala Met
    1010                1015                1020
Ser Thr Phe Tyr Gly Asn Gln Tyr His Asp Asp Pro Ser Pro Tyr Ala
1025                1030                1035                1040
Thr Thr Thr Leu Val Leu Ser Asn Gln Gln Pro Ala Trp Leu Asn Asp
                    1045                1050                1055
Lys Met Leu Arg Ala Pro Ala Met Pro Thr Asn Pro Val Pro Pro Glu
            1060                1065                1070
Pro Pro Ala Arg Tyr Ala Asp His Thr Ala Gly Arg Arg Ser Arg Ser
        1075                1080                1085
Ser Arg Ala Ser Asp Gly Arg Gly Thr Leu Asn Gly Gly Leu His His
    1090                1095                1100
Arg Thr Ser Gly Ser Gln Arg Ser Asp Ser Pro Pro His Thr Asp Val
1105                1110                1115                1120
Ser Tyr Val Gln Leu His Ser Ser Asp Gly Thr Gly Ser Ser Lys Glu
                1125                1130                1135
Arg Thr Gly Glu Arg Arg Thr Pro Pro Asn Lys Thr Leu Met Asp Phe
            1140                1145                1150
Ile Pro Pro Pro Pro Ser Asn Pro Pro Pro Gly Gly His Val Tyr
        1155                1160                1165
Asp Thr Ala Thr Arg Arg Gln Leu Asn Arg Gly Ser Thr Pro Arg Glu
```

```
       1170              1175             1180
Asp Thr Tyr Asp Ser Val Ser Asp Gly Ala Phe Ala Arg Val Asp Val
1185             1190              1195             1200
Asn Ala Arg Pro Thr Ser Arg Asn Arg Asn Leu Gly Gly Arg Pro Leu
            1205             1210              1215
Lys Gly Lys Arg Asp Asp Ser Gln Arg Ser Ser Leu Met Met Asp
1220              1225              1230
Asp Asp Gly Gly Ser Ser Glu Ala Asp Gly Glu Asn Ser Glu Gly Asp
        1235              1240              1245
Val Pro Arg Gly Val Arg Lys Ala Val Pro Arg Met Gly Ile Ser
1250              1255              1260
Ala Ser Thr Leu Ala His Ser Cys Tyr Gly Thr Asn Gly Thr Ala Gln
1265              1270              1275              1280
Arg Phe Arg Ser Ile Pro Arg Asn Asn Gly Ile Val Thr Gln Glu Gln
            1285              1290              1295
Thr
```

<210> SEQ ID NO 7
<211> LENGTH: 4956
<212> TYPE: DNA
<213> ORGANISM: human

<400> SEQUENCE: 7

```
atgaaatgga acatgttcc ttttttggtc atgatatcac tcctcagctt atccccaaat      60
cacctgtttc tggcccagct tattccagac cctgaagatg tagagagggg gaacgaccac     120
gggacgccaa tccccacctc tgataacgat gacaattcgc tgggctatac aggctcccgt     180
cttcgtcagg aagattttcc acctcgcatt gttgaacacc cttcagacct gattgtctca     240
aaaggagaac ctgcaacttt gaactgcaaa gctgaaggcc gccccacacc cactattgaa     300
tggtacaaag ggggagagag agtggagaca gacaaagatg accctcgctc acccgaatg      360
ttgctgccga gtggatcttt attttctta cgtatagtac atggacggaa agtagacct       420
gatgaaggag tctatgtctg tgtagcaagg aattaccttg agaggctgt gagccacaat      480
gcatcgctgg aagtagccat acttcgggat gacttcagac aaaaccctc ggatgtcatg      540
gttgcagtag agagcctgc agtaatggaa tgccaacctc cacgaggcca tcctgagccc      600
accatttcat ggaagaaaga tggctctcca ctggatgata agatgaaag aataactata      660
cgaggaggaa agctcatgat cacttacacc cgtaaaagtg acgctggcaa atatgtttgt     720
gttggtacca atatggttgg ggaacgtgag agtgaagtag ccgagctgac tgtcttagag     780
agaccatcat ttgtgaagag acccagtaac ttggcagtaa ctgtggatga cagtgcagaa     840
tttaaatgtg aggcccgagg tgaccctgta cctacagtac gatggaggaa agatgatgga     900
gagctgccca atccagata tgaaatccga atgatcata ccttgaaaat taggaaggtg      960
acagctggtg acatgggttc atacacttgt gttgcagaaa atatggtggg caaagctgaa    1020
gcatctgcta ctctgactgt tcaagaacct ccacattttg ttgtgaaacc ccgtgaccag    1080
gttgttgctt tgggacggac tgtaactttt cagtgtgaag caaccggaaa tcctcaacca    1140
gctatttttct ggaggagaga agggagtcag atctactttt ctcatatca accaccacag    1200
tcatccagcc gattttcagt ctcccagact ggcgacctca attactaa gtccagcga      1260
tctgatgttg ttattacat ctgccagact ttaaatgttg ctggaagcat catcacaaag    1320
gcatatttgg aagttacaga tgtgattgca gatcggcctc ccccagttat tcgacaaggt    1380
```

-continued

```
cctgtgaatc agactgtagc cgtggatggc actttcgtcc tcagctgtgt ggccacaggc    1440
agtccagtgc ccaccattct gtggagaaag gatggagtcc tcgtttcaac ccaagactct    1500
cgaatcaaac agttggagaa tggagtactg cagatccgat atgctaagct gggtgatact    1560
ggtcggtaca cctgcattgc atcaacccc agtggtgaag caacatggag tgcttacatt    1620
gaagttcaag aatttggagt tccagttcag cctccaagac ctactgaccc aaatttaatc    1680
cctagtgccc catcaaaacc tgaagtgaca gatgtcagca gaaatacagt cacattatcg    1740
tggcaaccaa atttgaattc aggagcaact ccaacatctt atattataga agccttcagc    1800
catgcatctg gtagcagctg gcagaccgta gcagagaatg tgaaaacaga acatctgcc    1860 attaaaggac tcaaacctaa tgcaatttac cttttccttg tgagggcagc taatgcatat    1920
ggaattagtg atccaagcca aatatcagat ccagtgaaaa cacaagatgt cctaccaaca    1980 agtcagggg tggaccacaa gcaggtccag agagagctgg gaaatgctgt tctgcacctc    2040
cacaacccca ccgtcctttc ttcctcttcc atcgaagtgc actggacagt agatcaacag    2100
tctcagtata tacaaggata taaaattctc tatcggccat ctggagccaa ccacggagaa    2160
tcagactggt tagttttga agtgaggacg ccagccaaaa acagtgtggt aatccctgat    2220
ctcagaaagg gagtcaacta tgaaattaag gctcgccctt tttttaatga atttcaagga    2280
gcagatagtg aaatcaagtt tgccaaaacc ctggaagaag cacccagtgc ccaccccaa    2340 ggtgtaactg tatccaagaa tgatggaaac ggaactgcaa ttctagttag ttggcagcca    2400
cctccagaag acactcaaaa tggaatggtc caagagtata aggtttggtg tctgggcaat    2460
gaaactcgat accacatcaa caaaacagtg gatggttcca ccttttccgt ggtcattccc    2520
tttcttgttc ctggaatccg atacagtgtg gaagtggcag ccagcactgg ggctgggtct    2580
ggggtaaaga gtgagcctca gttcatccag ctggatgccc atggaaaccc tgtgtcacct    2640
gaggaccaag tcagcctcgc tcagcagatt tcagatgtgg tgaagcagcc ggccttcata    2700
gcaggtattg gagcagcctg ttggatcatc ctcatggtct tcagcatctg gctttatcga    2760
caccgcaaga gagaaacgg acttactagt acctacgcgg gtatcagaaa agtcccgtct    2820
tttaccttca caccaacagt aacttaccag agaggaggcg aagctgtcag cagtggaggg    2880
aggcctggac ttctcaacat cagtgaacct gccgcgcagc catggctggc agacacgtgg    2940
cctaatactg gcaacaacca caatgactgc tccatcagct gctgcacggc aggcaatgga    3000
aacagcgaca gcaacctcac tacctacagt cgcccagctg attgtatagc aaattataac    3060
aaccaactgg ataacaaaca aacaaatctg atgctccctg agtcaactgt ttatggtgat    3120
gtggacctta gtaacaaaat caatgagatg aaaaccttca atagcccaaa tctgaaggat    3180
gggcgttttg tcaatccatc agggcagcct actccttacg ccaccactca gctcatccag    3240
tcaaacctca gcaacaacat gaacaatggc agcggggact ctggcagaa gcactggaaa    3300 ccactgggac agcagaaaca agaagtggca ccagttcagt acaacatcgt ggagcaaaac    3360
aagctgaaca aagattatcg agcaaatgac acagttcctc caactatccc atacaaccaa    3420
tcatacgacc agaacacagg aggatcctac aacagctcag accggggcag tagtacatct    3480
gggagtcagg ggcacaagaa aggggcaaga acacccaagg taccaaaaca gggtggcatg    3540
aactgggcag acctgcttcc tcctccccca gcacatcctc ctccacacag caatagcgaa    3600
gagtacaaca tttctgtaga tgaaagctat gaccaagaaa tgccatgtcc cgtgccacca    3660
gcaaggatgt atttgcaaca agatgaatta agaggaggag aagatgaacg aggccccact    3720 cccctgttc ggggagcagc ttcttctcca gctgccgtgt cctatagcca tcagtccact    3780
```

```
gccactctga ctccctcccc acaggaagaa ctccagccca tgttacagga ttgtccagag    3840
gagactggcc acatgcagca ccagcccgac aggagacggc agcctgtgag tcctcctcca    3900
ccaccacggc cgatctcccc tccacatacc tatggctaca tttcaggacc cctggtctca    3960
gatatggata cggatgcgcc agaagaggaa gaagacgaag ccgacatgga ggtagccaag    4020
atgcaaacca gaaggctttt gttacgtggg cttgagcaga cacctgcctc cagtgttggg    4080
gacctggaga gctctgtcac ggggtccatg atcaacggct ggggctcagc ctcagaggag    4140
gacaacattt ccagcggacg ctccagtgtt agttcttcgg acggctcctt tttcactgat    4200
gctgactttg cccaggcagt cgcagcagcg gcagagtatg ctggtctgaa agtagcacga    4260
cggcaaatgc aggatgctgc tggccgtcga cattttcatg cgtctcagtg ccctaggccc    4320
acaagtcccg tgtctacaga cagcaacatg agtgccgccg taatgcagaa aaccagacca    4380
gccaagaaac tgaaacacca gccaggacat ctgcgcagag aaacctacac agatgatctt    4440
ccaccacctc ctgtgccgcc acctgctata aagtcaccta ctgcccaatc caagacacag    4500
ctggaagtac gacctgtagt ggtgccaaaa ctccccttcta tggatgcaag aacagacaga    4560
tcatcagaca gaaaaggaag cagttacaag ggagagaag tgttggatgg aagacaggtt     4620
gttgacatgc gaacaaatcc aggtgatccc agagaagcac aggaacagca aaatgacggg    4680
aaaggacgtg gaaacaaggc agcaaaacga gaccttccac cagcaaagac tcatctcatc    4740
caagaggata ttctacctta ttgtagacct acttttccaa catcaaataa tcccagagat    4800
cccagttcct caagctcaat gtcatcaaga ggatcaggaa gcagacaaag agaacaagca    4860
aatgtaggtc gaagaaatat tgcagaaatg caggtacttg gaggatatga agaggagaa    4920 gataataatg aagaattaga ggaaactgaa agctga                              4956
```

<210> SEQ ID NO 8
<211> LENGTH: 1651
<212> TYPE: PRT
<213> ORGANISM: human

<400> SEQUENCE: 8

```
Met Lys Trp Lys His Val Pro Phe Leu Val Met Ile Ser Leu Leu Ser
 1               5                  10                  15

Leu Ser Pro Asn His Leu Phe Leu Ala Gln Leu Ile Pro Asp Pro Glu
             20                  25                  30

Asp Val Glu Arg Gly Asn Asp His Gly Thr Pro Ile Pro Thr Ser Asp
         35                  40                  45

Asn Asp Asp Asn Ser Leu Gly Tyr Thr Gly Ser Arg Leu Arg Gln Glu
     50                  55                  60

Asp Phe Pro Pro Arg Ile Val Glu His Pro Ser Asp Leu Ile Val Ser
 65                  70                  75                  80

Lys Gly Glu Pro Ala Thr Leu Asn Cys Lys Ala Glu Gly Arg Pro Thr
                 85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
    130                 135                 140

Tyr Val Cys Val Ala Arg Asn Tyr Leu Gly Glu Ala Val Ser His Asn
145                 150                 155                 160
```

```
Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val
305                 310                 315                 320

Thr Ala Gly Asp Met Gly Ser Tyr Thr Cys Val Ala Glu Asn Met Val
                325                 330                 335

Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
        355                 360                 365

Thr Phe Gln Cys Glu Ala Thr Gly Asn Pro Gln Pro Ala Ile Phe Trp
    370                 375                 380

Arg Arg Glu Gly Ser Gln Asn Leu Leu Phe Ser Tyr Gln Pro Pro Gln
385                 390                 395                 400

Ser Ser Ser Arg Phe Ser Val Ser Gln Thr Gly Asp Leu Thr Ile Thr
                405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
        435                 440                 445

Ile Ala Asp Arg Pro Pro Val Ile Arg Gln Gly Pro Val Asn Gln
450                 455                 460

Thr Val Ala Val Asp Gly Thr Phe Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
            500                 505                 510

Arg Tyr Ala Lys Leu Gly Asp Thr Gly Arg Tyr Thr Cys Ile Ala Ser
        515                 520                 525

Thr Pro Ser Gly Glu Ala Thr Trp Ser Ala Tyr Ile Glu Val Gln Glu
    530                 535                 540

Phe Gly Val Pro Val Gln Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
```

-continued

```
                    580                 585                 590
Ser Tyr Ile Ile Glu Ala Phe Ser His Ala Ser Gly Ser Ser Trp Gln
            595                 600                 605

Thr Val Ala Glu Asn Val Lys Thr Glu Thr Ser Ala Ile Lys Gly Leu
            610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                    645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
            675                 680                 685

Ser Ser Ile Glu Val His Trp Thr Val Asp Gln Gln Ser Gln Tyr Ile
            690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                    725                 730                 735

Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
            755                 760                 765

Lys Thr Leu Glu Glu Ala Pro Ser Ala Pro Pro Gln Gly Val Thr Val
770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
                    805                 810                 815

Cys Leu Gly Asn Glu Thr Arg Tyr His Ile Asn Lys Thr Val Asp Gly
            820                 825                 830

Ser Thr Phe Ser Val Val Ile Pro Phe Leu Val Pro Gly Ile Arg Tyr
            835                 840                 845

Ser Val Glu Val Ala Ala Ser Thr Gly Ala Gly Ser Gly Val Lys Ser
850                 855                 860

Glu Pro Gln Phe Ile Gln Leu Asp Ala His Gly Asn Pro Val Ser Pro
865                 870                 875                 880

Glu Asp Gln Val Ser Leu Ala Gln Gln Ile Ser Asp Val Val Lys Gln
                    885                 890                 895

Pro Ala Phe Ile Ala Gly Ile Gly Ala Ala Cys Trp Ile Ile Leu Met
                    900                 905                 910

Val Phe Ser Ile Trp Leu Tyr Arg His Arg Lys Lys Arg Asn Gly Leu
            915                 920                 925

Thr Ser Thr Tyr Ala Gly Ile Arg Lys Val Pro Ser Phe Thr Phe Thr
            930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
                    965                 970                 975

Ala Asp Thr Trp Pro Asn Thr Gly Asn Asn His Asn Asp Cys Ser Ile
            980                 985                 990

Ser Cys Cys Thr Ala Gly Asn Gly Asn Ser Asp Ser Asn Leu Thr Thr
            995                 1000                1005
```

```
Tyr Ser Arg Pro Ala Asp Cys Ile Ala Asn Tyr Asn Asn Gln Leu Asp
    1010                1015                1020
Asn Lys Gln Thr Asn Leu Met Leu Pro Glu Ser Thr Val Tyr Gly Asp
1025                1030                1035                1040
Val Asp Leu Ser Asn Lys Ile Asn Glu Met Lys Thr Phe Asn Ser Pro
                1045                1050                1055
Asn Leu Lys Asp Gly Arg Phe Val Asn Pro Ser Gly Gln Pro Thr Pro
            1060                1065                1070
Tyr Ala Thr Thr Gln Leu Ile Gln Ser Asn Leu Ser Asn Asn Met Asn
        1075                1080                1085
Asn Gly Ser Gly Asp Ser Gly Glu Lys His Trp Lys Pro Leu Gly Gln
    1090                1095                1100
Gln Lys Gln Glu Val Ala Pro Val Gln Tyr Asn Ile Val Glu Gln Asn
1105                1110                1115                1120
Lys Leu Asn Lys Asp Tyr Arg Ala Asn Asp Thr Val Pro Pro Thr Ile
                1125                1130                1135
Pro Tyr Asn Gln Ser Tyr Asp Gln Asn Thr Gly Gly Ser Tyr Asn Ser
            1140                1145                1150
Ser Asp Arg Gly Ser Ser Thr Ser Gly Ser Gln Gly His Lys Lys Gly
        1155                1160                1165
Ala Arg Thr Pro Lys Val Pro Lys Gln Gly Gly Met Asn Trp Ala Asp
    1170                1175                1180
Leu Leu Pro Pro Pro Ala His Pro Pro His Ser Asn Ser Glu
1185                1190                1195                1200
Glu Tyr Asn Ile Ser Val Asp Glu Ser Tyr Asp Gln Glu Met Pro Cys
                1205                1210                1215
Pro Val Pro Pro Ala Arg Met Tyr Leu Gln Gln Asp Glu Leu Glu Glu
            1220                1225                1230
Glu Glu Asp Glu Arg Gly Pro Thr Pro Pro Val Arg Gly Ala Ala Ser
        1235                1240                1245
Ser Pro Ala Ala Val Ser Tyr Ser His Gln Ser Thr Ala Thr Leu Thr
    1250                1255                1260
Pro Ser Pro Gln Glu Glu Leu Gln Pro Met Leu Gln Asp Cys Pro Glu
1265                1270                1275                1280
Glu Thr Gly His Met Gln His Gln Pro Asp Arg Arg Arg Gln Pro Val
                1285                1290                1295
Ser Pro Pro Pro Pro Arg Pro Ile Ser Pro Pro His Thr Tyr Gly
            1300                1305                1310
Tyr Ile Ser Gly Pro Leu Val Ser Asp Met Asp Thr Asp Ala Pro Glu
    1315                1320                1325
Glu Glu Glu Asp Glu Ala Asp Met Glu Val Ala Lys Met Gln Thr Arg
1330                1335                1340
Arg Leu Leu Leu Arg Gly Leu Glu Gln Thr Pro Ala Ser Ser Val Gly
1345                1350                1355                1360
Asp Leu Glu Ser Ser Val Thr Gly Ser Met Ile Asn Gly Trp Gly Ser
                1365                1370                1375
Ala Ser Glu Glu Asp Asn Ile Ser Ser Gly Arg Ser Ser Val Ser Ser
            1380                1385                1390
Ser Asp Gly Ser Phe Phe Thr Asp Ala Asp Phe Ala Gln Ala Val Ala
        1395                1400                1405
Ala Ala Ala Glu Tyr Ala Gly Leu Lys Val Ala Arg Arg Gln Met Gln
    1410                1415                1420
```

```
Asp Ala Ala Gly Arg Arg His Phe His Ala Ser Gln Cys Pro Arg Pro
1425                1430                1435                1440

Thr Ser Pro Val Ser Thr Asp Ser Asn Met Ser Ala Ala Val Met Gln
            1445                1450                1455

Lys Thr Arg Pro Ala Lys Lys Leu Lys His Gln Pro Gly His Leu Arg
        1460                1465                1470

Arg Glu Thr Tyr Thr Asp Leu Pro Pro Pro Val Pro Pro Pro
    1475                1480                1485

Ala Ile Lys Ser Pro Thr Ala Gln Ser Lys Thr Gln Leu Glu Val Arg
    1490                1495                1500

Pro Val Val Pro Lys Leu Pro Ser Met Asp Ala Arg Thr Asp Arg
1505                1510                1515                1520

Ser Ser Asp Arg Lys Gly Ser Ser Tyr Lys Gly Arg Glu Val Leu Asp
            1525                1530                1535

Gly Arg Gln Val Val Asp Met Arg Thr Asn Pro Gly Asp Pro Arg Glu
        1540                1545                1550

Ala Gln Glu Gln Gln Asn Asp Gly Lys Gly Arg Gly Asn Lys Ala Ala
        1555                1560                1565

Lys Arg Asp Leu Pro Pro Ala Lys Thr His Leu Ile Gln Glu Asp Ile
    1570                1575                1580

Leu Pro Tyr Cys Arg Pro Thr Phe Pro Thr Ser Asn Asn Pro Arg Asp
1585                1590                1595                1600

Pro Ser Ser Ser Ser Ser Met Ser Ser Arg Gly Ser Gly Ser Arg Gln
            1605                1610                1615

Arg Glu Gln Ala Asn Val Gly Arg Arg Asn Ile Ala Glu Met Gln Val
        1620                1625                1630

Leu Gly Gly Tyr Glu Arg Gly Glu Asp Asn Asn Glu Glu Leu Glu Glu
        1635                1640                1645

Thr Glu Ser
    1650

<210> SEQ ID NO 9
<211> LENGTH: 854
<212> TYPE: DNA
<213> ORGANISM: human

<400> SEQUENCE: 9
cagattgttg ctcaaggtcg aacagtgaca tttccctgtg aaactaaagg aaacccacag    60
ccagctgttt tttggcagaa agaaggcagc cagaacctac ttttcccaaa ccaaccccag   120
cagcccaaca gtagatgctc agtgtcacca actggagacc tcacaatcac caacattcaa   180
cgttccgacg cgggttacta catctgccag gctttaactg tggcaggaag cattttagca   240
aaagctcaac tggaggttac tgatgttttg acagatagac ctccacctat aattctacaa   300
ggcccagcca accaaacgct ggcagtggat ggtacagcgt tactgaaatg taaagccact   360
ggtgatcctc ttcctgtaat tagctggtta aaggagggat ttacttttcc gggtagagat   420
ccaagagcaa caattcaaga gcaaggcaca ctgcagatta agaatttacg gatttctgat   480
actggcactt atacttgtgt ggctacaagt tcaagtggag aggcttcctg gagtgcagtg   540
ctggatgtga cagagtctgg agcaacaatc agtaaaaact atgatttaag tgacctgcca   600
gggccaccat ccaaaccgca agtcactgat gttactaaga acagtgtcac cttgtcctgg   660
cagccaggta cccctggaac ccttccagca agtgcatata tcattgaggc tttcagccaa   720
tcagtgagca acagctggca gaccgtggca aaccatgtaa agaccaccct ctatactgta   780
```

```
agaggactgc ggcccaatac aatctactta ttcatggtca gagcgatcaa ccccaaggty    840
tcagtgaccc aagt                                                      854

<210> SEQ ID NO 10
<211> LENGTH: 284
<212> TYPE: PRT
<213> ORGANISM: human

<400> SEQUENCE: 10
```

Gln Ile Val Ala Gln Gly Arg Thr Val Thr Phe Pro Cys Glu Thr Lys
  1               5                  10                  15

Gly Asn Pro Gln Pro Ala Val Phe Trp Gln Lys Glu Gly Ser Gln Asn
                 20                  25                  30

Leu Leu Phe Pro Asn Gln Pro Gln Pro Asn Ser Arg Cys Ser Val
             35                  40                  45

Ser Pro Thr Gly Asp Leu Thr Ile Thr Asn Ile Gln Arg Ser Asp Ala
 50                  55                  60

Gly Tyr Tyr Ile Cys Gln Ala Leu Thr Val Ala Gly Ser Ile Leu Ala
 65                  70                  75                  80

Lys Ala Gln Leu Glu Val Thr Asp Val Leu Thr Asp Arg Pro Pro
                 85                  90                  95

Ile Ile Leu Gln Gly Pro Ala Asn Gln Thr Leu Ala Val Asp Gly Thr
            100                 105                 110

Ala Leu Leu Lys Cys Lys Ala Thr Gly Asp Pro Leu Pro Val Ile Ser
            115                 120                 125

Trp Leu Lys Glu Gly Phe Thr Phe Pro Gly Arg Asp Pro Arg Ala Thr
130                 135                 140

Ile Gln Glu Gln Gly Thr Leu Gln Ile Lys Asn Leu Arg Ile Ser Asp
145                 150                 155                 160

Thr Gly Thr Tyr Thr Cys Val Ala Thr Ser Ser Ser Gly Glu Ala Ser
                165                 170                 175

Trp Ser Ala Val Leu Asp Val Thr Glu Ser Gly Ala Thr Ile Ser Lys
            180                 185                 190

Asn Tyr Asp Leu Ser Asp Leu Pro Gly Pro Ser Lys Pro Gln Val
            195                 200                 205

Thr Asp Val Thr Lys Asn Ser Val Thr Leu Ser Trp Gln Pro Gly Thr
210                 215                 220

Pro Gly Thr Leu Pro Ala Ser Ala Tyr Ile Ile Glu Ala Phe Ser Gln
225                 230                 235                 240

Ser Val Ser Asn Ser Trp Gln Thr Val Ala Asn His Val Lys Thr Thr
                245                 250                 255

Leu Tyr Thr Val Arg Gly Leu Arg Pro Asn Thr Ile Tyr Leu Phe Met
            260                 265                 270

Val Arg Ala Ile Asn Pro Lys Val Ser Val Thr Gln
            275                 280

```
<210> SEQ ID NO 11
<211> LENGTH: 444
<212> TYPE: DNA
<213> ORGANISM: mouse

<400> SEQUENCE: 11
gcccaggcag ttgctgcagc tgcggagtat gcgggcctga agtggctcg ccgccaaatg   60 caagatgctg ctggccgccg ccacttccat gcctctcagt gcccaggcc cacgagtcct  120 gtgtccacag acagcaacat gagtgctgtt gtgatccaga aagccagacc cgccaagaag  180
```

```
cagaaacacc agccaggaca tctgcgcagg gaagcctacg cagatgatct tccacccct     240 ccagtgccac cacctgctat aaaatcgccc actgtccagt ccaaggcaca gctggaggta    300
cggcctgtca tggtgccaaa actcgcgtct atagaagcaa ggacagatag atcgtcagac    360
agaaaaggag gcagttacaa ggggagagaa gctctggatg gaagacaagt cactgacctg    420
cgaacaaatc caagtgaccc caga                                            444
```

```
<210> SEQ ID NO 12
<211> LENGTH: 148
<212> TYPE: PRT
<213> ORGANISM: mouse

<400> SEQUENCE: 12
```

```
Ala Gln Ala Val Ala Ala Ala Glu Tyr Ala Gly Leu Lys Val Ala
 1               5                  10                  15

Arg Arg Gln Met Gln Asp Ala Ala Gly Arg Arg His Phe His Ala Ser
                20                  25                  30

Gln Cys Pro Arg Pro Thr Ser Pro Val Ser Thr Asp Ser Asn Met Ser
            35                  40                  45

Ala Val Val Ile Gln Lys Ala Arg Pro Ala Lys Lys Gln Lys His Gln
        50                  55                  60

Pro Gly His Leu Arg Arg Glu Ala Tyr Ala Asp Asp Leu Pro Pro Pro
 65                  70                  75                  80

Pro Val Pro Pro Ala Ile Lys Ser Pro Thr Val Gln Ser Lys Ala
                85                  90                  95

Gln Leu Glu Val Arg Pro Val Met Val Pro Lys Leu Ala Ser Ile Glu
                100                 105                 110

Ala Arg Thr Asp Arg Ser Ser Asp Arg Lys Gly Gly Ser Tyr Lys Gly
            115                 120                 125

Arg Glu Ala Leu Asp Gly Arg Gln Val Thr Asp Leu Arg Thr Asn Pro
        130                 135                 140

Ser Asp Pro Arg
145
```

```
<210> SEQ ID NO 13
<211> LENGTH: 1781
<212> TYPE: DNA
<213> ORGANISM: Drosophila melanogaster

<400> SEQUENCE: 13
tgagtgcctc gcccacgact cactcaagag cgagtgaatc gagaaaatga gtgagtggaa     60
tggcaaattt cccgcatggc atggcattct cagcgacccg atgtaggtat tatgctctgc    120
cagctagcag tcagtcaact tatagccgct ccagcgaacg gacgcaccga aaatcgagct    180
atagaaactc tacggcaaat aaaaaaaccc gaaatcgaac ccatgactta tatatagagc    240
caaacgattt gtttacgtgt cgtgacgcga gtgtgccagc agttgtgtgc gtgtgccaga    300
cgcaagcaga aaataaagtt tacaaattaa aataaatcaa aggcaatcac catgattagc    360
accacggatt atccaacggt ggagaccacc acaactgccg aagagctcta tgcggagtac    420
atatccgcgc cggccagcag catgagtccc gctgcaattg ccgagcacct gcagcagaat    480
cagatcacct tcgagatacc cagtgcccac gatctgcgac acatcgacgc cctcaactcc    540
ttcaacgccc tgctccagag gattggcaac gcagcggtgt cctacgatcc cgctccaccc    600
agcggctggt ctccggatgg cagcatcagc accgagcagc tctccaagtc ggtggttctg    660
```

-continued

```
gatctggccg acttgcggga taggtccgag gaatcgggcg aatcctcgtg gtggagccag      720
atcttcgggg atgccgacat gcatgtgatc atcaattatc tgtggatcgg agtggtcagc      780
tcgctggtca ttctgtcgct ggtcttcatc ctcttcagct gctacttcta caggaagttc      840
cgcacttgga aaaatgcaa taaggacata cgtgcccaga tccatgcggc cagtgactcg       900
tactcctcgc acctggttgg ttgcgatgcc agcagactgc tgttgcacca gcagatgcag      960
catccacatc atcggagcag cgaggctggg ttctaccaaa tcgaatcgcc gccctgctac     1020
acaatcgcca ccggattgcc cagctacgat gaggcactgc atcatcagcc tcggcacttt     1080
gcctacggca tgaagttcgt ttatccctcg ttggcggccg tgcatcatca tcaccattgc     1140
atttccaatt gggagaagca ggagccgctg aataagctgc aaaagtgcaa gctgtcagcg     1200
gcagcggcag tggaggagga taaagccgac tcctcatcgt ccacgtctgc atccgcgtcg     1260
ccatcctctt cggaatccag caacttggcc acagcaacgc ctgccatttg cattaacatg     1320
ccaagtgggc ggcaggatga ggaggtggat aattcagatt ccgattccgc aattgcagtt     1380
gcagtggcag tagcacaaag tttacagccg gcggcgcctg ccgacgatga ttgcgcctca     1440
ttggtcgttg ttgttgccgc gtgattgccc acccaggggt cagaggtcag ggaataaggg     1500
gtcagtcgag ggtttagggc cgggagtagc agcccaattg cttagtcact tgtaaatagt     1560
tgcatcgtct gctaatgttg tttgccccat gtaataacat atatctccga gaatgtaccc     1620
tctccctccc tctaagaaaa tttagttttg gttttagtt atctgttata tattattgta      1680
ttacgcaaga ctgagtatta tttattgtac tatgtataaa accgaattgt ctatcgatta     1740
agccctaata tctaagcgag agttgaagaa aaaatataaa a                          1781
```

<210> SEQ ID NO 14
<211> LENGTH: 370
<212> TYPE: PRT
<213> ORGANISM: Drosophila melanogaster

<400> SEQUENCE: 14

```
Met Ile Ser Thr Thr Asp Tyr Pro Thr Val Glu Thr Thr Thr Thr Ala
  1               5                  10                  15

Glu Glu Leu Tyr Ala Glu Tyr Ile Ser Ala Pro Ala Ser Ser Met Ser
             20                  25                  30

Pro Ala Ala Ile Ala Glu His Leu Gln Gln Asn Gln Ile Thr Phe Glu
         35                  40                  45

Ile Pro Ser Ala His Asp Leu Arg His Ile Asp Ala Leu Asn Ser Phe
     50                  55                  60

Asn Ala Leu Leu Gln Arg Ile Gly Asn Ala Ala Val Ser Tyr Asp Pro
 65                  70                  75                  80

Ala Pro Pro Ser Gly Trp Ser Pro Asp Gly Ser Ile Ser Thr Glu Gln
                 85                  90                  95

Leu Ser Lys Ser Val Val Leu Asp Leu Ala Asp Leu Arg Asp Arg Ser
            100                 105                 110

Glu Glu Ser Gly Glu Ser Ser Trp Trp Ser Gln Ile Phe Gly Asp Ala
        115                 120                 125

Asp Met His Val Ile Ile Asn Tyr Leu Trp Ile Gly Val Val Ser Ser
    130                 135                 140

Leu Val Ile Leu Ser Leu Val Phe Ile Leu Phe Ser Cys Tyr Phe Tyr
145                 150                 155                 160

Arg Lys Phe Arg Thr Trp Lys Lys Cys Asn Lys Asp Ile Arg Ala Gln
                165                 170                 175
```

Ile His Ala Ala Ser Asp Ser Tyr Ser His Leu Val Gly Cys Asp
            180                 185                 190

Ala Ser Arg Leu Leu His Gln Gln Met Gln His Pro His His Arg
            195                 200                 205

Ser Ser Glu Ala Gly Phe Tyr Gln Ile Glu Ser Pro Pro Cys Tyr Thr
    210                 215                 220

Ile Ala Thr Gly Leu Pro Ser Tyr Asp Glu Ala Leu His His Gln Pro
225                 230                 235                 240

Arg His Phe Ala Tyr Gly Met Lys Phe Val Tyr Pro Ser Leu Ala Ala
                245                 250                 255

Val His His His His His Cys Ile Ser Asn Trp Glu Lys Gln Glu Pro
            260                 265                 270

Leu Asn Lys Leu Gln Lys Cys Lys Leu Ser Ala Ala Ala Val Glu
            275                 280                 285

Glu Asp Lys Ala Asp Ser Ser Ser Thr Ser Ala Ser Ala Ser Pro
290                 295                 300

Ser Ser Ser Glu Ser Ser Asn Leu Ala Thr Ala Thr Pro Ala Ile Cys
305                 310                 315                 320

Ile Asn Met Pro Ser Gly Arg Gln Asp Glu Glu Val Asp Asn Ser Asp
                325                 330                 335

Ser Asp Ser Ala Ile Ala Val Ala Val Ala Val Ala Gln Ser Leu Gln
            340                 345                 350

Pro Ala Ala Pro Ala Asp Asp Cys Ala Ser Leu Val Val Val Val
            355                 360                 365

Ala Ala
    370

<210> SEQ ID NO 15
<211> LENGTH: 330
<212> TYPE: DNA
<213> ORGANISM: human

<400> SEQUENCE: 15
aaaccacaga aaacaatgg atccacttgg gccaatgtcc ctctacctcc cccccagtc      60 cagcccttc ctggcacgga gctggaacac tatgcagtgg aacaacaaga aaatggctat   120
gacagtgata gctggtgccc accattgcca gtacaaactt acttacacca aggtctggaa   180
gatgaactgg aagaagatga tgatagggtc ccaacacctc ctgttcgagg cgtggcttct   240
tctcctgcta tctcctttgg acagcagtcc actgcaactc ttactccatc cccacgggaa   300
gagatgcaac ccatgctgca ggcttcacct                                     330

<210> SEQ ID NO 16
<211> LENGTH: 114
<212> TYPE: DNA
<213> ORGANISM: human

<400> SEQUENCE: 16
tttacctcct ctcaaagacc tcgacctacc agcccatttt ctactgacag taacaccagt    60
gcagccctga gtcaaagtca gaggcctcgg cccactaaaa acacaagggg aggg          114

<210> SEQ ID NO 17
<211> LENGTH: 110
<212> TYPE: PRT
<213> ORGANISM: human

<400> SEQUENCE: 17

-continued

```
Lys Pro Gln Lys Asn Asn Gly Ser Thr Trp Ala Asn Val Pro Leu Pro
 1               5                  10                 15

Pro Pro Pro Val Gln Pro Leu Pro Gly Thr Glu Leu Glu His Tyr Ala
             20              25                  30

Val Glu Gln Gln Glu Asn Gly Tyr Asp Ser Asp Ser Trp Cys Pro Pro
         35              40                  45

Leu Pro Val Gln Thr Tyr Leu His Gln Gly Leu Glu Asp Glu Leu Glu
     50                  55                  60

Glu Asp Asp Asp Arg Val Pro Thr Pro Pro Val Arg Gly Val Ala Ser
65                  70                  75                  80

Ser Pro Ala Ile Ser Phe Gly Gln Gln Ser Thr Ala Thr Leu Thr Pro
                 85                  90                  95

Ser Pro Arg Glu Glu Met Gln Pro Met Leu Gln Ala Ser Pro
                100             105                 110

<210> SEQ ID NO 18
<211> LENGTH: 38
<212> TYPE: PRT
<213> ORGANISM: human

<400> SEQUENCE: 18

Phe Thr Ser Ser Gln Arg Pro Arg Pro Thr Ser Pro Phe Ser Thr Asp
 1               5                  10                 15

Ser Asn Thr Ser Ala Ala Leu Ser Gln Ser Gln Arg Pro Arg Pro Thr
             20                  25                  30

Lys Lys His Lys Gly Gly
             35
```